United States Patent
Iger et al.

(10) Patent No.: US 11,779,758 B2
(45) Date of Patent: *Oct. 10, 2023

(54) APPARATUS AND METHOD OF NON-INVASIVE DIRECTIONAL TISSUE TREATMENT

(71) Applicant: DASYO TECHNOLOGY LTD, Rosh-HaAyin (IL)

(72) Inventors: Yoni Iger, Haifa (IL); Dan David Albeck, Givat Shmuel (IL)

(73) Assignee: DASYO TECHNOLOGY LTD, Rosh-Haayin (IL)

( * ) Notice: Subject to any disclaimer, the term of this patent is extended or adjusted under 35 U.S.C. 154(b) by 61 days.

This patent is subject to a terminal disclaimer.

(21) Appl. No.: 17/546,055

(22) Filed: Dec. 9, 2021

(65) Prior Publication Data
US 2022/0096828 A1    Mar. 31, 2022

Related U.S. Application Data

(63) Continuation of application No. 16/177,481, filed on Nov. 1, 2018, now Pat. No. 11,666,754, which is a
(Continued)

(51) Int. Cl.
*A61N 1/32* (2006.01)
*A61B 18/18* (2006.01)
(Continued)

(52) U.S. Cl.
CPC .......... *A61N 1/328* (2013.01); *A61B 18/1206* (2013.01); *A61B 18/1402* (2013.01); *A61B 18/18* (2013.01); *A61N 1/0404* (2013.01); *A61N 1/06* (2013.01); *A61B 2018/0016* (2013.01); *A61B 2018/0047* (2013.01); *A61B 2018/00577* (2013.01); *A61B 2018/00589* (2013.01); *A61B 2018/00642* (2013.01);
(Continued)

(58) Field of Classification Search
CPC ....... A61N 1/238; A61N 1/0404; A61B 18/18
See application file for complete search history.

(56) References Cited

U.S. PATENT DOCUMENTS 6,350,276 B1    2/2002 Knowlton
11,129,982 B2 *  9/2021 Iger .................... A61B 18/1402
(Continued)

FOREIGN PATENT DOCUMENTS

WO    WO2013/076714    5/2013
WO    WO2013/168051    11/2013

OTHER PUBLICATIONS

Extended European Search Report for EP Application No. 16796012.9, dated Dec. 10, 2018.
(Continued)

*Primary Examiner* — Kaitlyn E Smith
(74) *Attorney, Agent, or Firm* — PEARL COHEN ZEDEK LATZER BARATZ LLP

(57) ABSTRACT

An apparatus for non-invasive directional tissue treatment comprises an energy source and an array of energy delivery elements placed in a predetermined order defining a tissue treatment area such that tissue tightening obtained is higher in a first direction than in a second direction of the two-dimensional array.

18 Claims, 23 Drawing Sheets

Related U.S. Application Data continuation of application No. 15/811,754, filed on Nov. 14, 2017, now Pat. No. 11,129,982, which is a continuation-in-part of application No. PCT/IL2016/050499, filed on May 11, 2016.

(60) Provisional application No. 62/421,391, filed on Nov. 14, 2016, provisional application No. 62/244,971, filed on Oct. 22, 2015, provisional application No. 62/161,969, filed on May 15, 2015.

(51) Int. Cl.
*A61N 1/04* (2006.01)
*A61B 18/14* (2006.01)
*A61B 18/12* (2006.01)
*A61N 1/06* (2006.01)
*A61N 1/40* (2006.01)
*A61B 18/00* (2006.01)

(52) U.S. Cl.
CPC ............... *A61B 2018/00702* (2013.01); *A61B 2018/00791* (2013.01); *A61B 2018/00875* (2013.01); *A61B 2018/124* (2013.01); *A61B 2018/1467* (2013.01); *A61N 1/40* (2013.01)

(56) References Cited

U.S. PATENT DOCUMENTS

| | | |
|---|---|---|
| 2004/0210214 A1 | 10/2004 | Knowlton |
| 2007/0088413 A1 | 4/2007 | Weber et al. |
| 2007/0142885 A1 | 6/2007 | Hantash et al. |
| 2008/0188846 A1 | 8/2008 | Palanker et al. |
| 2009/0270788 A1 | 10/2009 | Marenus et al. |
| 2011/0034912 A1 | 2/2011 | De Graff et al. |
| 2011/0218464 A1 | 9/2011 | Iger |
| 2012/0185029 A1 | 7/2012 | Flyash et al. |
| 2012/0310311 A1 | 12/2012 | Elkah |
| 2013/0226269 A1 | 8/2013 | Eckhouse et al. |
| 2013/0282085 A1 | 10/2013 | Lischinsky et al. |
| 2013/0289679 A1 | 10/2013 | Echhouse et al. |
| 2013/0331913 A1 | 12/2013 | Levi et al. |
| 2014/0249609 A1 | 9/2014 | Zarsky et al. |
| 2015/0038965 A1 | 2/2015 | Iger |

OTHER PUBLICATIONS

International Search Report of PCT Application No. PCT/IL2016/050499, dated Aug. 21, 2016.
Office Action for U.S. Appl. No. 15/811,754, dated Apr. 2, 2020.
Office Action for U.S. Appl. No. 15/811,754, dated Dec. 22, 2020.
Notice of Acceptance for U.S. Appl. No. 15/811,754, dated May 28, 2021.
Office Action for U.S. Appl. No. 16/177,481, dated May 26, 2021.
Office Action for U.S. Appl. No. 15/811,754, dated Sep. 17, 2020.

\* cited by examiner

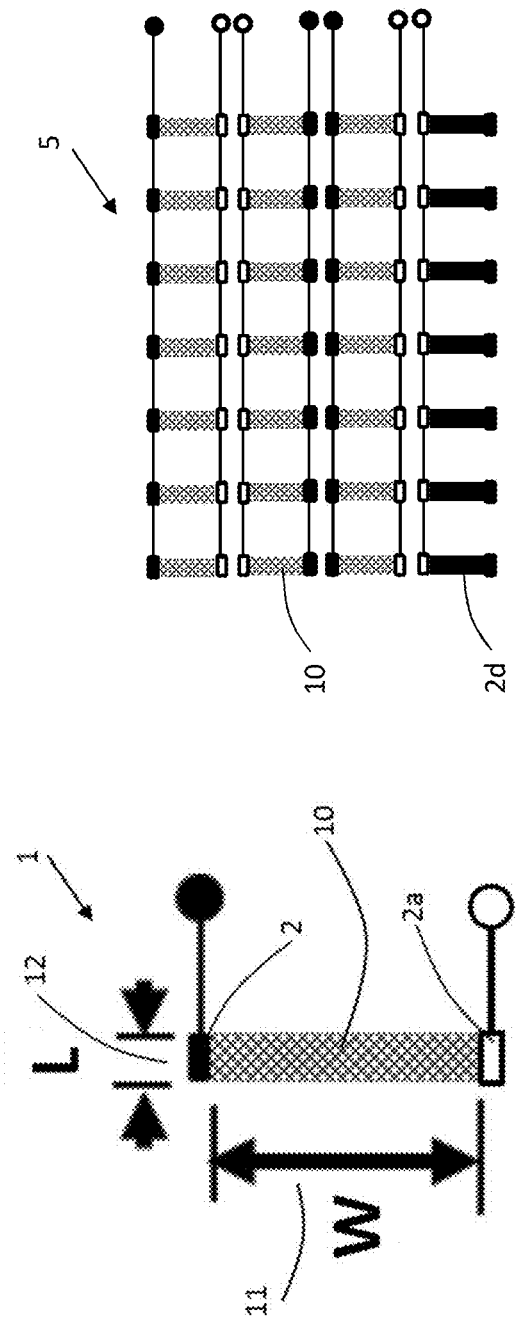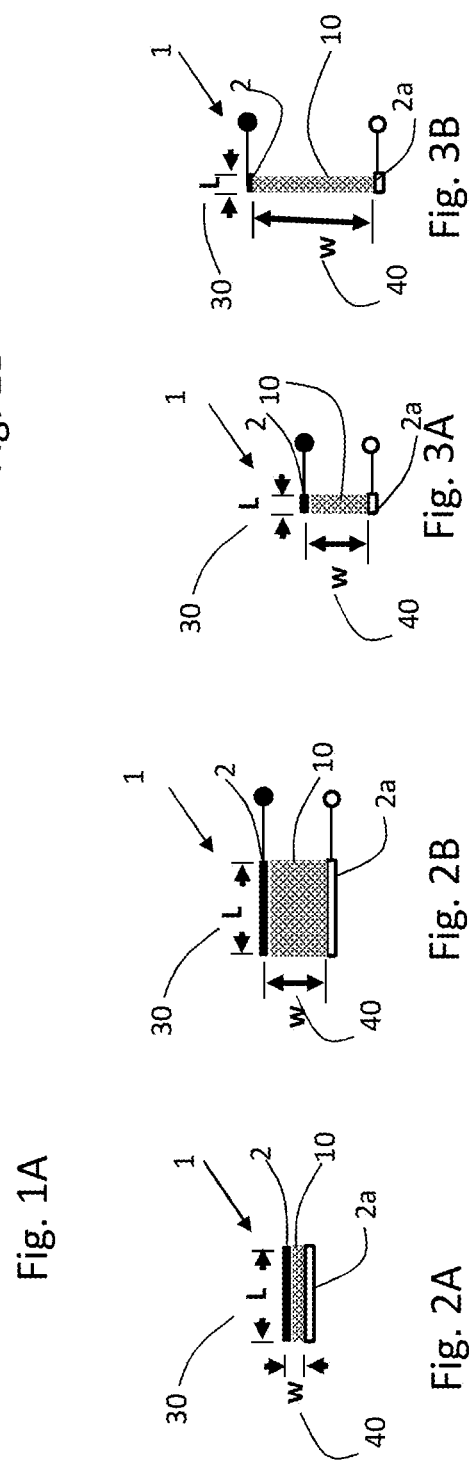

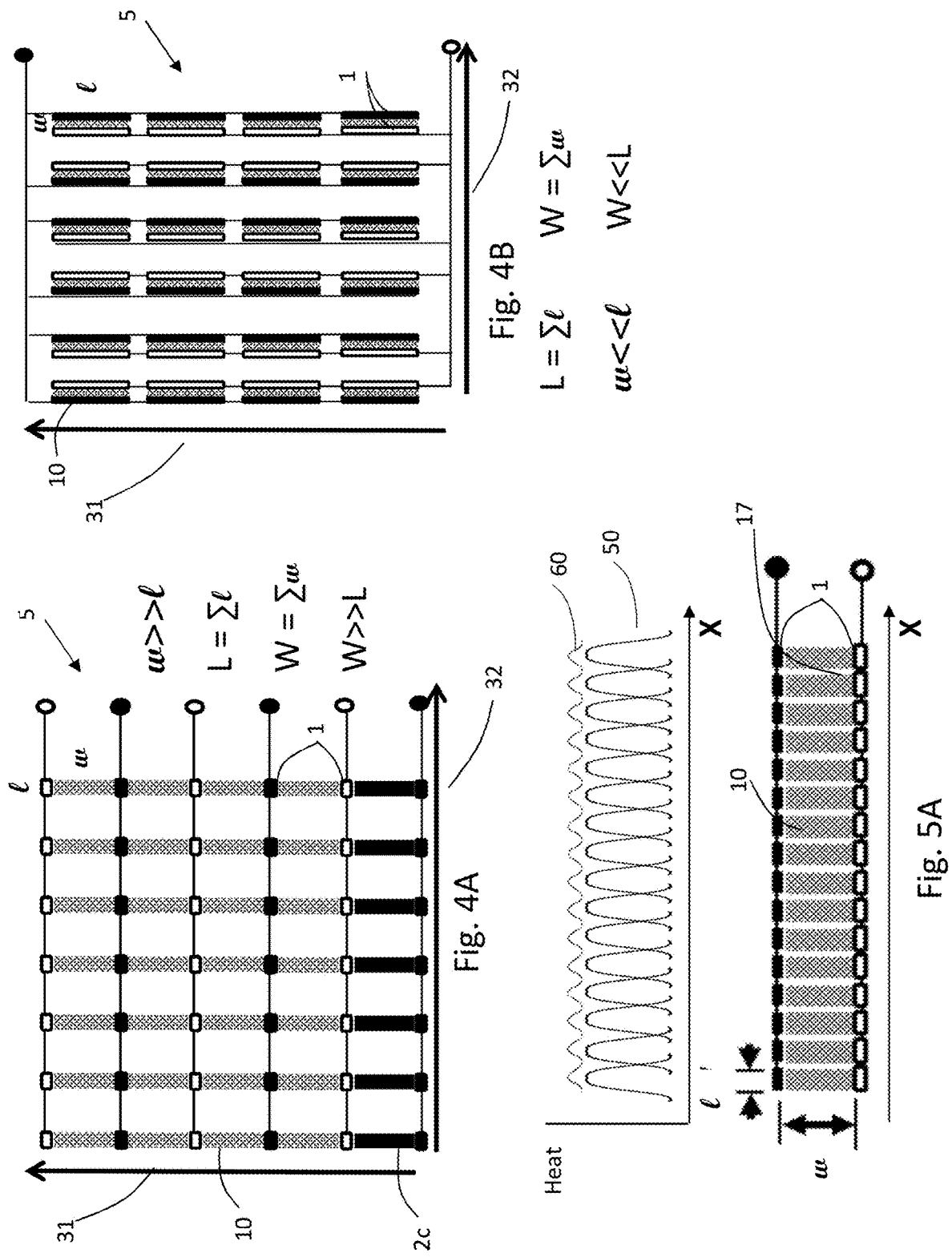

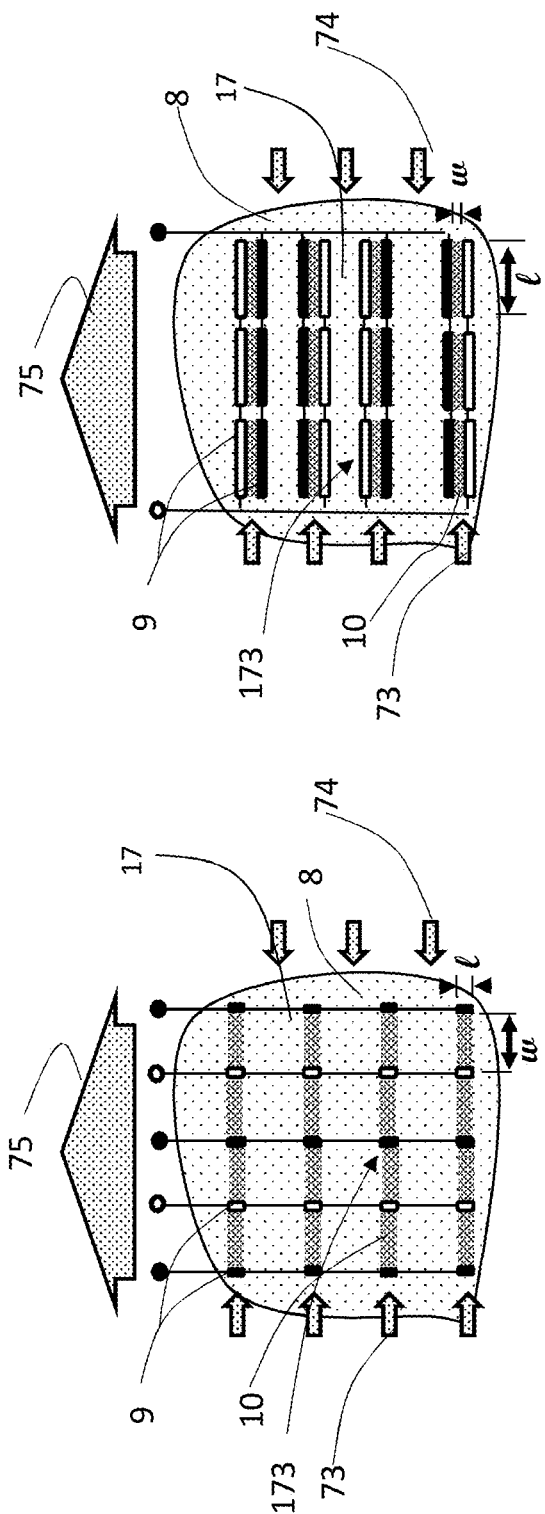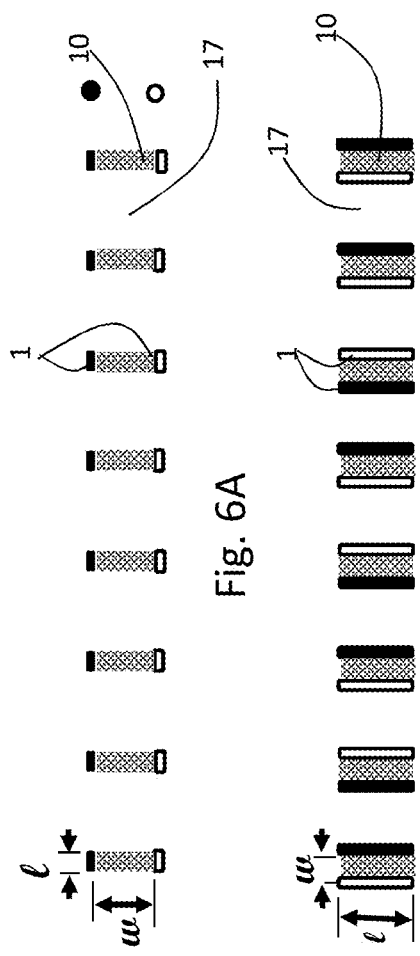

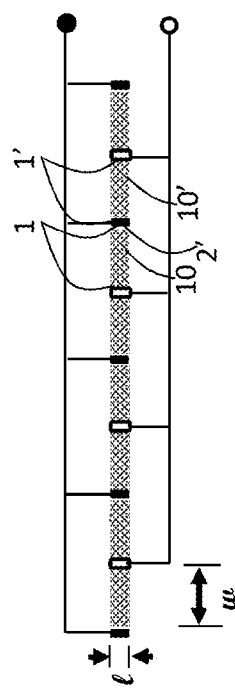
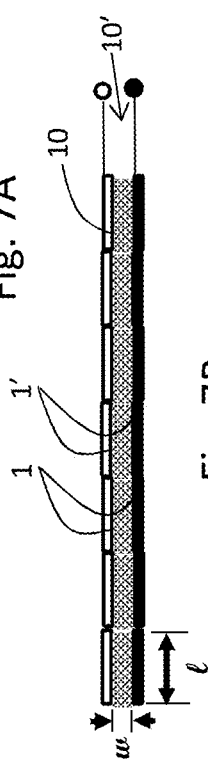
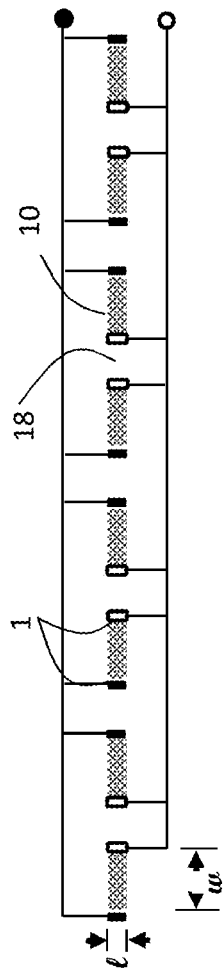
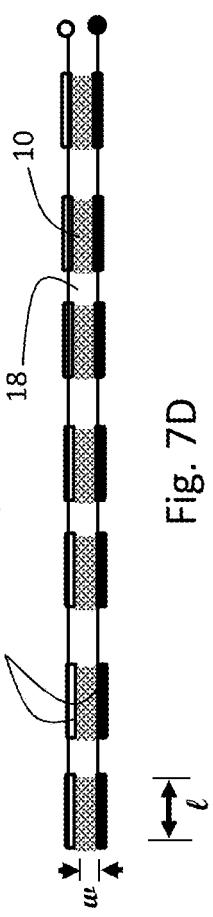

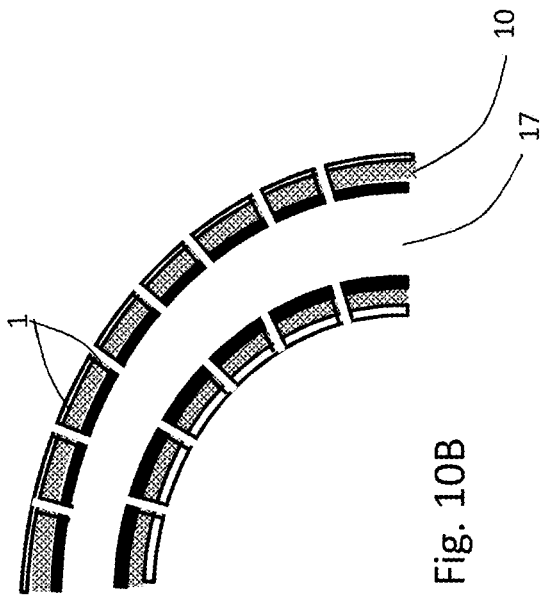
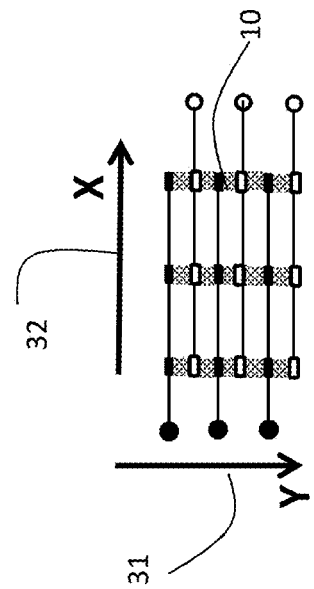
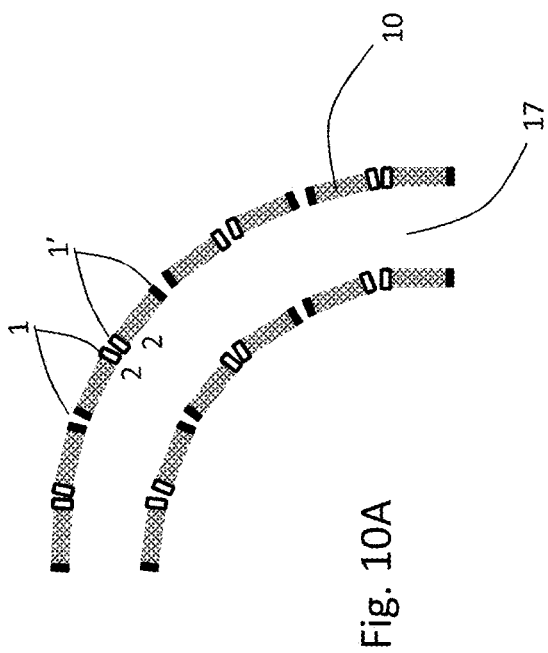
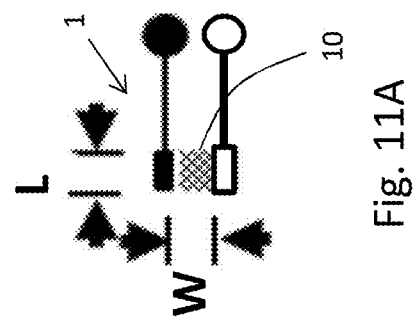
Fig. 10A
Fig. 10B
Fig. 11A
Fig. 11B

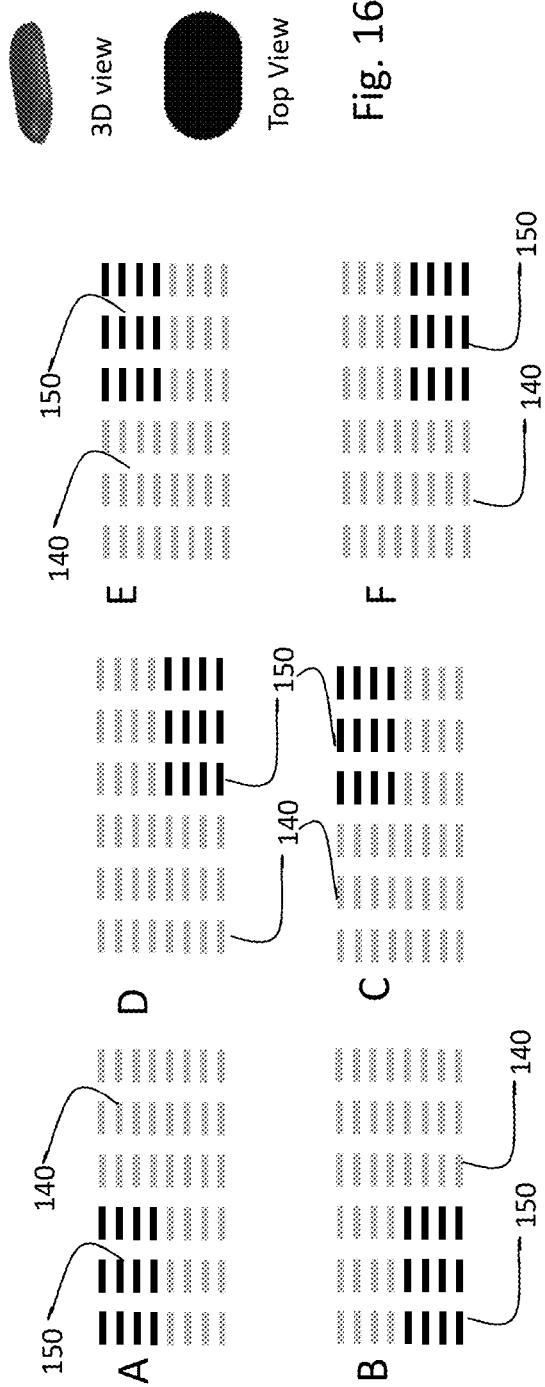

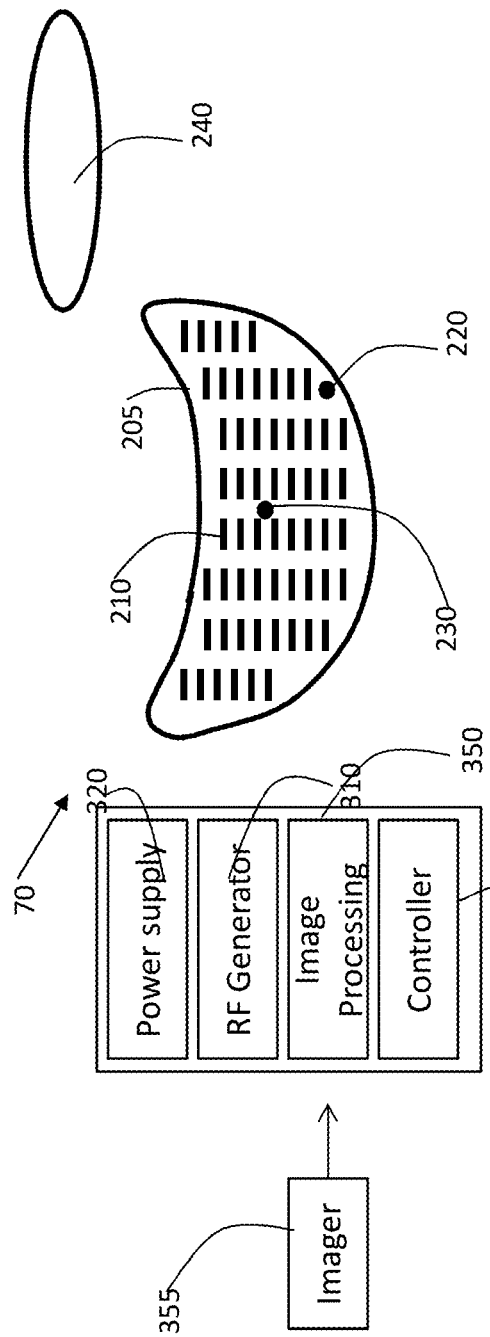

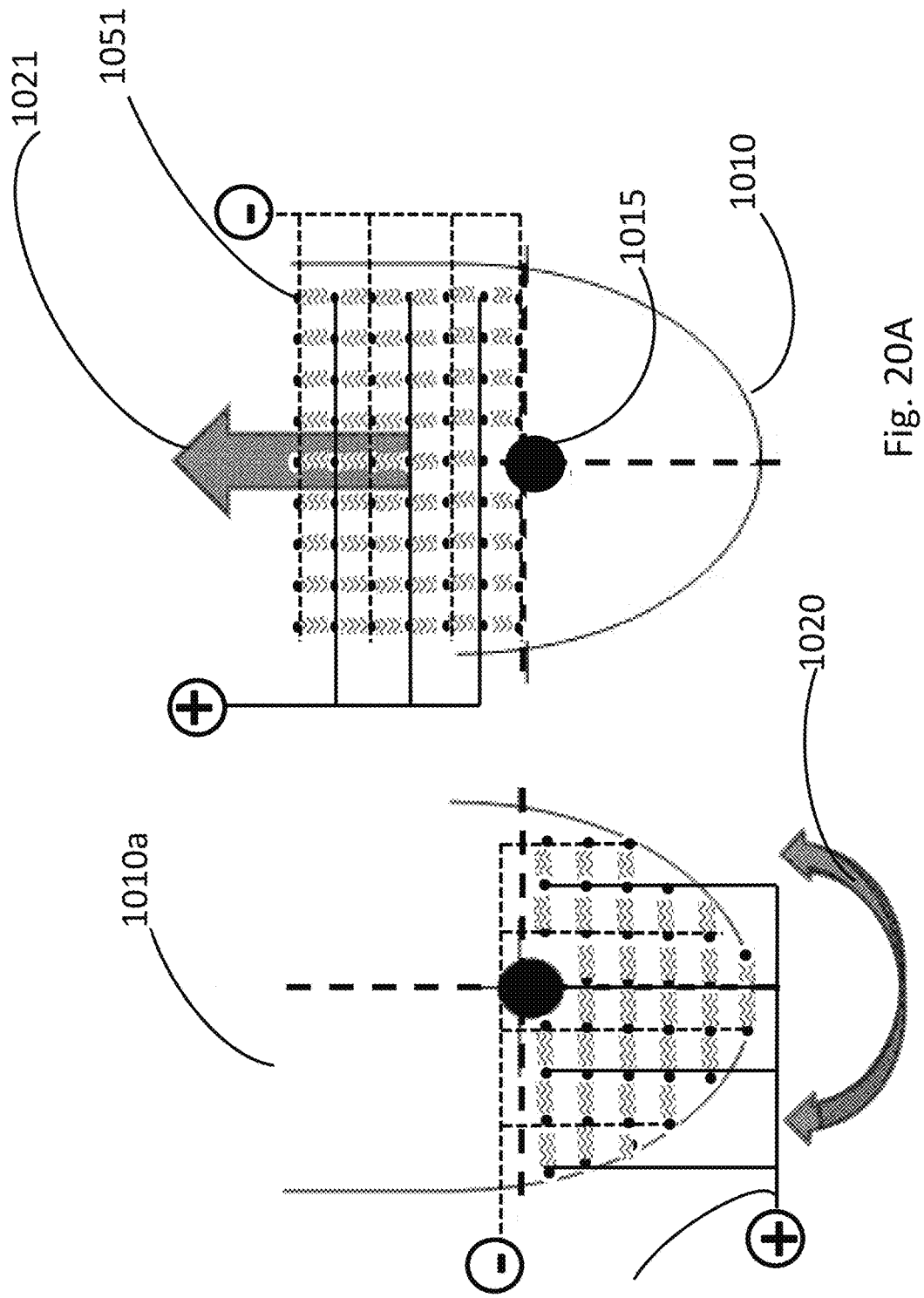

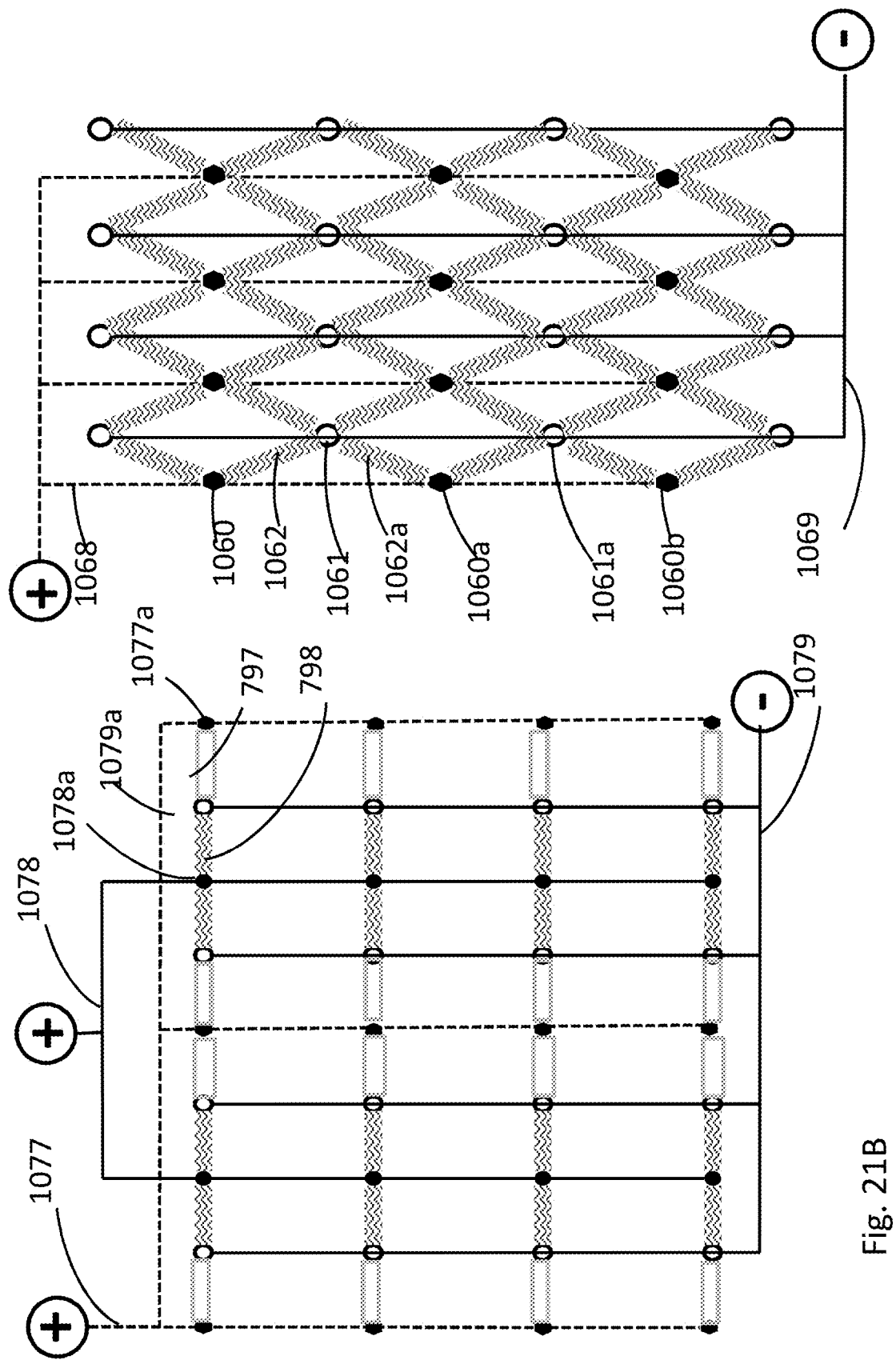

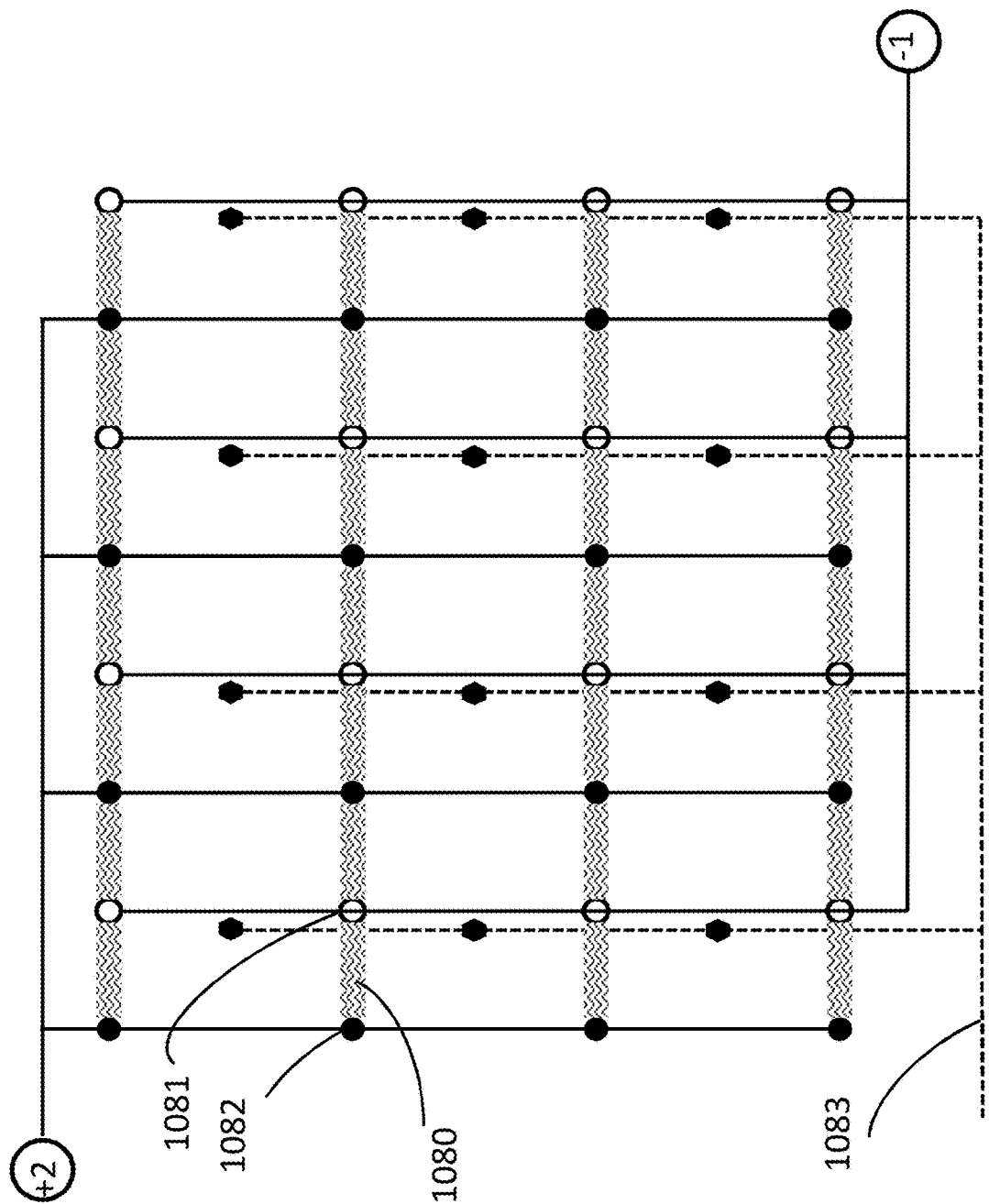

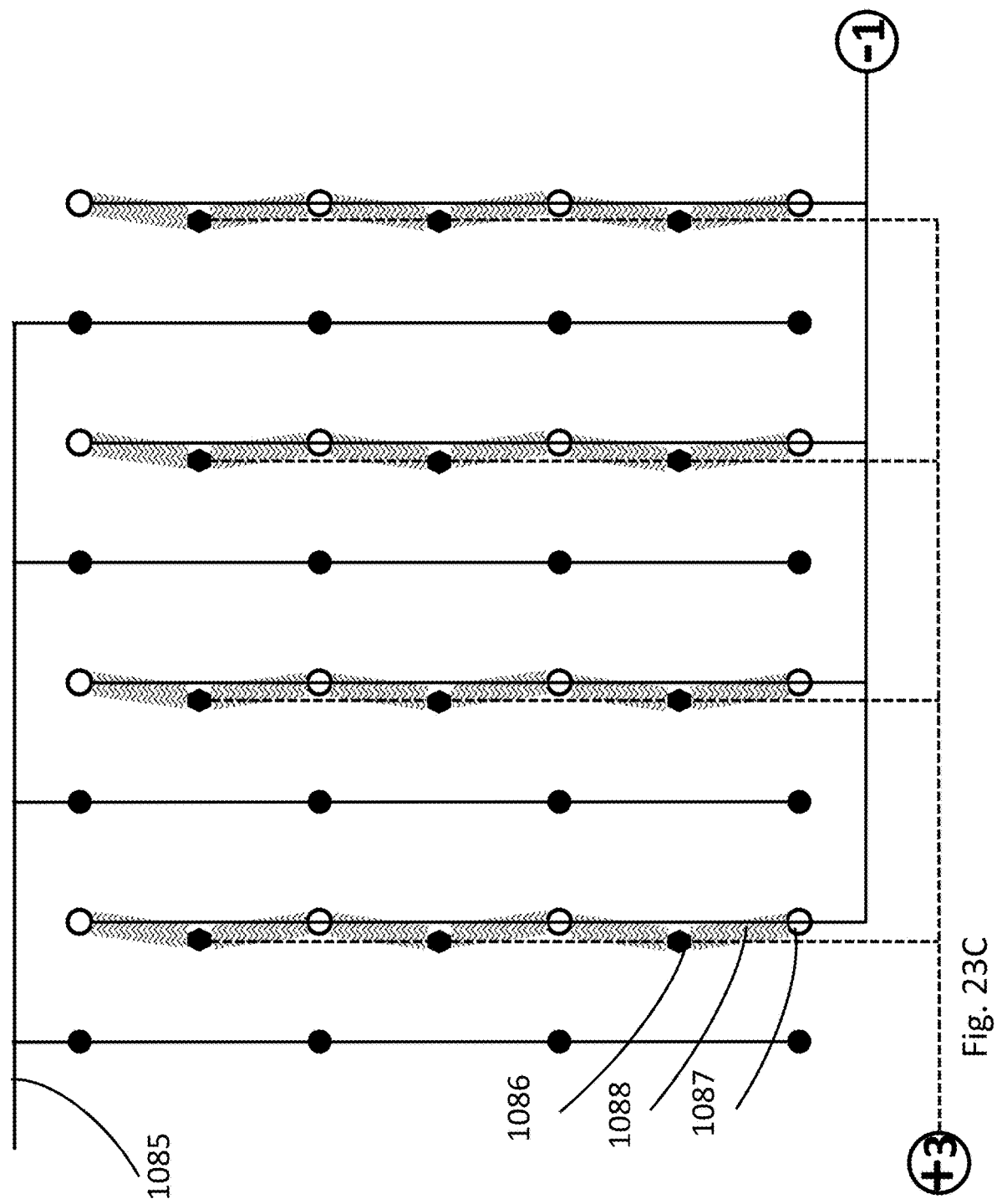

APPARATUS AND METHOD OF NON-INVASIVE DIRECTIONAL TISSUE TREATMENT

CROSS REFERENCE TO RELATED APPLICATIONS

This application is a continuation of U.S. application Ser. No. 16/177,481, filed Nov. 1, 2018, which is a continuation of U.S. patent application Ser. No. 15/811,754, filed on Nov. 14, 2017, now U.S. Pat. No. 11,129,982, which is a continuation in part of International Patent Application No. PCT/IL2016/050499 filed on May 11, 2016, which claims the benefit of U.S. Provisional Application No. 62/161,969, filed on May 15, 2015, and U.S. Provisional Application No. 62/244,971, filed Oct. 22, 2015; U.S. patent application Ser. No. 15/811,754 claims the benefit of U.S. Provisional Application No. 62/421,391, filed on Nov. 14, 2016, all of which are incorporated in their entirety herein by reference.

BACKGROUND OF THE INVENTION

The field of body contouring and tissue tightening has grown very rapidly over the past several years, with many new devices appearing on the market that utilize radiofrequency (RF) energy to safely and effectively tighten and rejuvenate the skin.

For successful delivery and transfer of the RF energy into thermal energy, different parameters must be considered including the size and depth of the tissue being treated, as the tissue impedance of the tissue being treated affects the actual heat transfer. RF energy in the form of electrical current through the tissue can be designed to have different heat impact and penetration depths in the tissue allowing for formation of different desired effects at different tissues at different desired depth.

Different parameters are known to affect RF current passage via tissues, and the derived heat impacts in tissue. RF frequency, RF current level and time duration, pulse mode including pulse modulation and inter-pulse delay, distance between electrodes, level of electrodes protrusion to the tissue and the like are among these influencing factors. The RF impact derived from RF current flowing in and via tissue having electric impedance, is being a tissue zone that is volumetrically heated to a level of tissue stimulation, coagulation or ablation and their combination.

Various RF bipolar configurations per-se or with the combination of other modalities like ultrasound, vacuum apparatus, electro-optical energy and the like allow deeper RF current penetration under the skin thus addressing rhytids, sagginess concerns and vascular problems.

Multipolar (e.g. triple, 4, 5, 6, 7, 8 electrical poles) RF energy configurations are used in an attempt to continue to deliver enough RF energy to be effective in skin rejuvenation and tissue tightening. By using multiple electrical poles, lower energies can be delivered into the skin from each electrical pole, making the treatments superior to the original monopolar. Multi-frequency RF energy devices to treat different depths are also in use.

Fractional bipolar RF works as other fractional devices in a way that the targeted areas being treated are benefited from the vitality of the skipped (e.g. untreated) areas adjacent to the affected skin portions to heal the skin faster than traditional resurfacing methods. This configuration of fractional ablative RF was used to access deep into the skin, by applying high RF current density using very small diameter electrodes and/or using protruded electrodes, to cause a rejuvenation response.

Monopolar RF configurations are also being used mainly for treatment of deep sub dermal layers. In these configurations the generated currents flow through the tissue from one or more electrodes, all with the same electrical polarity to a grounding or "return" electrode, and meets maximum resistance in proximity the tip of the electrodes, where tissue heating in the deep dermal or sub dermal layers then occurs. For example, such a treatment may include the grounding or "return pad" attached to the patient's lower back or abdomen, to provide a low resistance path for the current to flow back to the treatment generator, to complete the electrical circuit The above products and treatment procedures commonly involve employing an applicator to house and translate the source of the application energy over the skin, following various patterns of translation paths in an attempt to have a spatial uniform treatment over the treated zone of the skin. The resultant effect, mostly tightening, tends to be homogeneous in its nature. This is applied and has benefit when same impact is desired over the entire treatment area and such an impact is conducted in 3D (three dimensional) orientation, so impact has no dominated direction. This may be useful for instance for treatment of early stage skin ptosis, where the slight 3D tightening may be sufficient to establish firmer and tighter look and feel of the skin.

At times it is desired to translate the source of the application energy over the skin, following various patterns of translation paths in an attempt to have a non-uniform spatial treatment, but rather a treatment that has a preferred orientation and/or a directional intensity distribution. The resultant effect, for example tightening, is not homogeneous and being applied more in certain direction as compared to other direction. This may have benefits when the application of higher or lower impact is desired in a directional treatment of an area. This may be useful, for instance, for treatment of advance stages of skin ptosis of different body organs, where the directional impact of gravity on the organs may be of greater effect as compared to overall non-directional loosening of tissue structure. Some medical conditions that may benefit from such treatment may be, for instance breast ptosis, facial droopy appearance, forehead wrinkles, loosened underarms and the like. Occasionally, such directional impact may be required to fight other disorders, not of gravitation origin. This applies, for instance for ageing effects on natural fold such as the facial nasolabial folds or the marionette line folds having a desired dominated direction of required tightening.

Directional tightening may be achieved by impacting the tissue non-uniformly with significantly different heat distribution in one direction as compared to the heat distribution in the other directions. This can be done in both micro and macro levels to result in a homogenous or degraded directional tightening as will be described herein.

As with all other tissues, time affects also breasts. Drooping or sagging female breast, manifest them as breast involution, with glandular volume loss, loose connective tissue support, extended fascia-skin envelope and ligaments, and loss of elasticity. At the phenotype level ptosis is characterized by a downward (when female is in an upward sitting or standing position) descent of the nipple position together with some descending of entire breast mass. Accordingly, the ptosis scale of mild, moderate, advanced and severe ptosis represents the location of the nipple relative to the infra-mammary fold. Pseudoptosis is when there is altered distribution of entire parenchyma breast mass, descending to the lower part of the breast with less to no impact on nipple position.

Both ptosis and pseudoptosis may start already at the 20s and are a natural consequence of aging with prevalence of 100%. It is affected or influenced by intrinsic factors such as hormonal changes during pregnancy and menopause leading to atrophies of glandular components, less cellular connective tissue and diminished collagen. Other intrinsic factors that affect breast sagginess are Body Mass Index (BMI), overweight or weight loss, breast cup size and age. Ptosis and pseudoptosis are also affected by extrinsic factors, including exposure to the dreaded pull of gravity and smoking.

Breast ptosis and pseudoptosis for women, loose skin and sagging appearance of face, submental and chin, underarm, abdomen or buttocks of both genders are not a health issue but an aesthetic issue that may adversely affects women's/men's self-image, confidence and self-esteem. It is therefore that efforts have been conducted for women and men of wide range of ages to turn toward younger appearance and image.

Methods for changing the breast appearance toward younger look are based on the basic anatomical fact that the breast is a "floating" organ, not having or not connected by muscles or any significant connective tissue or bones. Current methods for such rejuvenation of size, contour and position of breasts sub anatomies such as nipples use invasive or minimal invasive modalities to reshape the breast pocket. It includes surgical procedures for breast lift or breast augmentation, invasive implant and positioning of threads, or minimal invasive RF derived heating procedures. For the purpose of presentation of the previous art and the current invention, each right or left breast is schematically divided to upper and lower anatomical poles, each composed of two quarters of the breast, for example, the lower anatomical pole includes the lower left and the lower right quarters of a breast.

During common breast lift, mastopexy, surgeon make incision around the areola, then vertically down from the areola to the breast crease and horizontally along the breast crease along the interface of the lower breast pole and the chest. Then excess breast skin is removed from the lower breast pole, the two edges of the skin cut are sutured, and the entire breast mass is positioned upward to compensate for its volume loss and loss of elasticity. In addition to reshaping to improve contour and firmness, the nipple and areola may be repositioned to an upper, more youthful height. In general, mastopexy procedure raises, contours, and firms the entire breast by surgically impacting the lower pole of the breast.

Another method for breast lifting is by reshaping it using internal scaffold, mostly made of barbed/cogged threads. Surgeon makes 8-20 trocars insertions into the subcutaneous fat layer, and each trocar is tunneled along predetermined plane, having an exit point at its end. The barbed/cogged threads, designed to hook into the subcutaneous tissues, are inserted into the end of the trocar and pulled through it out of the opposite exit point. The trocar is then removed, and the thread is slightly pulled for reshaping of breast, tugged gently, hooked into the subcutaneous tissue, stabilized and trimmed. Threads reconstruct the breast shape and stimulate collagen synthesis around them.

Energy-based methods have also been conducted to treat breast ptosis. During such procedure. RF cannula with a tip that emits RF energy is inserted under the breast skin. The inserted cannula, which acts against a second on-surface electrode, is run back and forth under the skin while emitting RF. During this process the emitted RF heats up the fibrous connective tissue of the breast fascia and dermis, located between the electrodes. When applied above a certain threshold, it coagulates collagen and other extra-cellular matrices. This results in collagen shrinkage and collagen tightening and phenotype of 3D breast tightening and lifting.

The above techniques are invasive, and are associated with significant risks—from anesthesia, bleeding or hematoma formation, infection, poor healing of incisions, changes in breast or nipple sensation, breast contour and shape irregularities or asymmetry, fat necrosis, fluid accumulation, deep vein thrombosis, and the like. Additionally, people in general, are reluctant to go through invasive procedures when not medically needed. Moreover, due to the invasiveness nature of the current methods people with low grade ptosis, pseudo-ptosis or low grade loosened skin don't tend to be treated to maintain a more youthful appearance.

There is a need to improve the appearance of drooped or pseudo drooped breast or loosened other anatomies using less traumatic and non-invasive methods and modalities. Furthermore, due to the intimal nature of the treatment it will be advantageous to do it at home comfort, using home-use-device (HUD).

SUMMARY OF THE INVENTION

Some embodiments of the invention may be related to an apparatus for non-invasive directional tissue treatment. The apparatus may include: a radiofrequency (RF) generator and an array of RF energy delivery elements in active communication with the RF generator, a power source and a controller. In some embodiments, each of the RF energy delivery elements may include a pair of electrodes with opposite polarity or having a monopolar configuration such that each electrode may have a first dimension and a second dimension, the first dimension perpendicular to the second dimension and to an imaginary line connecting the pair of electrodes to each other. In some embodiments, the first dimension of each electrode and the distance between the electrodes in each pair may be configured to create an elongated heated volume of tissue when the RF generator may be activated and at least one of the RF delivery elements is in contact with the tissue.

Some additional embodiments of the invention may be related to a method of non-invasive directional tissue treatment. The method may include setting a treatment protocol and attaching at least a portion of an array of RF emitting elements, powered by an RF generator, to an area of the tissue to be treated. The method may further include activating the RF generator and deactivating the RF generator by a controller, based on the treatment protocol. In some embodiments, each of the RF energy delivery elements may include a pair of electrodes with opposite polarity or having a monopolar configuration, such that each electrode may have a first dimension and a second dimension, the first dimension perpendicular to the second dimension and to an imaginary line connecting the pair of electrodes to each other. In some embodiments, the first dimension of each electrode and the distance between the electrodes in each pair may be configured to create an elongated heated volume of tissue when the RF generator may be activated and at least one of the RF delivery elements is in contact with the tissue.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 1A is a schematic illustration of a radiofrequency (RF) delivery element according to one embodiment of the present invention;

FIG. 1B illustrates an array of RF delivery elements according to some embodiments of the present invention;

FIGS. 2A. 2B, 3A and 3B illustrate different configurations of RF delivery elements according to embodiments of the present invention:

FIGS. 4A and 4B are schematic illustrations of layouts of arrays according to some embodiments of the present invention;

FIG. 5A is an illustration of arrays of RF energy delivery elements according to some embodiments of the invention;

FIGS. 5B and 5C are illustrations of examples for tightening impact and parallel elongated bipolar pairs according to some embodiments of the invention;

FIGS. 6A and 6B are illustrations of exemplary electrode configurations according to some embodiments of the invention;

FIGS. 7A-7D are illustrations of additional exemplary electrode configurations according to some embodiments of the invention;

FIGS. 10A and 10B illustrate 2D (two dimensional) arrays of RF delivery elements according to some embodiments of the invention;

FIG. 11A is an illustration of an RF delivery element according to some embodiments of the invention;

FIG. 11B is an illustration of an array of RF delivery elements according to some embodiments of the invention;

FIG. 15 is an illustration of a schematic operation method of an array of RF delivery elements according some embodiments of the invention;

FIG. 16 is an image of an electrode according to some embodiments of the invention;

FIG. 17A is an illustration of an apparatus for non-invasive directional tissue treatment according to some embodiments of the invention.

FIGS. 20 and 20A illustrate an RF delivery elements array and wiring according to embodiments of the present invention;

FIGS. 21A and 21B is an illustrations of electrodes array and wiring for achieving a non-continuous tightening impact according to some embodiments of the invention;

FIGS. 23A-23C are illustrations of electrodes arrays to support several treatment directions according to some embodiments of the inventions;

Figure 8:
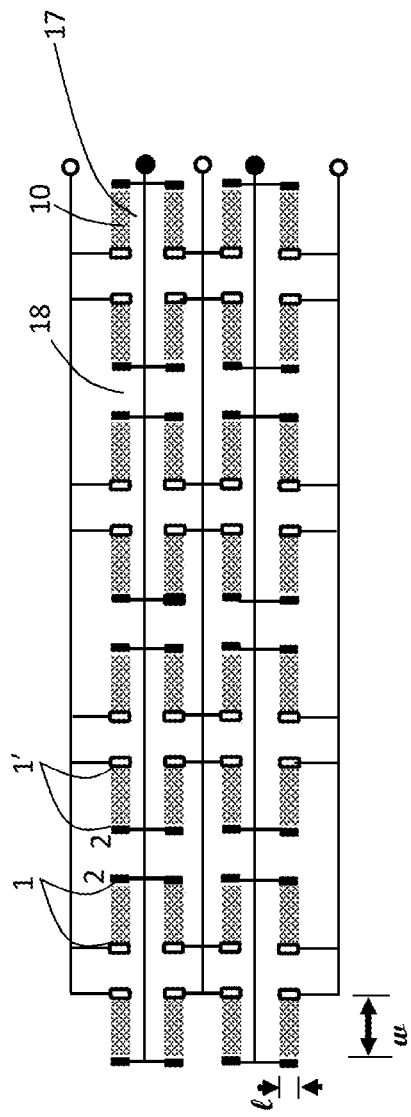
FIG. 8 is an illustration of an array of RF delivery elements according to some embodiments of the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Although embodiments of the invention are not limited in this regard, discussions utilizing terms such as, for example, "processing," "computing," "calculating," "determining," "establishing", "analyzing", "checking", or the like, may refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory storage medium that may store instructions to perform operations and/or processes. Although embodiments of the invention are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. The term set when used herein may include one or more items. Unless explicitly stated, the method embodiments described herein are not constrained to a particular order or sequence. Additionally, some of the described method embodiments or elements thereof can occur or be performed simultaneously, at the same point in time, or concurrently.

Some embodiments of the present invention may provide method and device, using fractionally delivered RF to form directional impacts on the tissue, RF delivery elements and arrays for providing such directional impacts and image based diagnosis to affect treatment procedure of such directional impact.

Embodiments of the present invention provide an apparatus and method for non-invasive directional tissue treatment. The treatment may include directionally heating soft tissues to cause an impact on the tissue. The impact may include any effect of heating of soft tissue, for example, coagulation of collagen and other extra-cellular matrix, collagen shrinkage and phenotype of collagen tightening, tissue tightening and shrinkage, and the like. According to some embodiments, the method may be based on fractional delivery of RF energy, using noninvasive electrodes embedded in tissue attachable patches/flex, while forming controllable (e.g., directional) treated volumes of tissue.

As used in this application, and in addition to its regular meaning, the term 'treated volume of tissue' may refer to a portion of tissue heated by one or more pairs of electrodes or heated by an elongated monopolar electrode. The treated volume of tissue may have a first dimension that may be substantially equal to the inter-electrode spacing (i.e. the distance between the electrodes in a pair of electrodes), a second dimension and a third dimension (e.g. width and depth) that may derive from the dimensions of a face of an electrode directed towards the other electrode in a pair of electrodes or the dimensions of the elongated monopolar electrode. The depth of the treated volume of tissue may be further affected from the inter-electrode spacing. In some embodiments, treated volume may be formed by applying RF current with predetermined parameters between a pair of bipolar electrodes of a predetermined configuration and inter-electrode spacing and each treatment volume may be heated to levels of stimulation, coagulation, ablation and their combinations.

The treated volumes may be of different dimensions, different predetermined orientations and inter-volume spacing, and may be formed at different tissue depth.

In some embodiments, assuming homogenous tissue and homogeneous heating, the impact on the tissue, such as tightening, may be directly correlated with the treated volumetric dimensions. Consequently, tissue tightening measure may be substantially directly proportional to the treated volume dimensions. As a result, tightening measure of elongated treated volumes may also have an elongated shape. Longer and narrower volumetric impact may result in higher unidirectional absolute impact phenomena such as tightening. The volumetric impact may be defined as the volume of the tissue that is impacted by the application of the RF energy by at least one energy delivery element. The volume of the impacted tissue may be larger than the treated volume due to heat dissipation and other tightening effects discussed below.

In some embodiments, in order to achieve directional impact such as tightening, the treated volumes and their distribution over the tissue may be designed to have significant different dimension values (e.g., impact dimension values) in one direction compared to another directions (e.g. orthogonal direction). This may be achieved both at the micro level value (e.g., the dimension of a volume treated by a single pair of RF electrodes) and in accumulated dimensions value of the overall treated volumes at the macro level.

An apparatus according to some embodiments of the invention may include, a radiofrequency (RF) generator (illustrated and discussed with respect to FIG. 17A) and an array of RF energy delivery elements in active communication with the RF generator. Each of the RF energy delivery elements may include a pair of electrodes with opposite polarity, to form the treated (impact) volume by applying RF energy to the electrodes and forming electric currents in the volume of a tissue treated by the pair of electrodes. In some embodiments, the array of RF energy delivery elements may include a plurality of monopolar electrodes all being in electrical connection with at least one current collector via the tissue. The volume of the tissue treated by the pair of electrodes or the monopolar electrode may depend on the dimensions of the electrodes, the distance between the electrodes in the pair, and the like.

In some embodiments, each electrode may have a first dimension and a second dimension, the first dimension perpendicular to the second dimension and to an imaginary line connecting the pair of electrodes to each other. In some embodiments, the first dimension of each electrode and the distance between the electrodes in each pair may be configured to create an elongated heated volume of the tissue when the RF generator is activated and at least one of the RF delivery elements is in contact with the tissue.

An exemplary energy delivery element 1 that includes a pair of electrodes is described in FIG. 1A. FIG. 1A is an illustration of an exemplary pair of electrodes 2 and 2a having opposite polarity. Electrodes 2 and 2a may have a length L and are placed in distance W from each other, such that W is perpendicular to L. In some embodiments, delivery element 1 may include a single monopolar electrode 2d (illustrated in FIG. 1B). A tissue treated (e.g., heated) volume 10 may be dimensionally non-uniform, have significant different dimension in direction 11 (e.g. parallel to the distance W) as compared to direction 12 (e.g. parallel to the width L). This form of treatment may result in an elongated treated volume of tissue. The aspect ratio W/L of the two dimensions may be >1 (larger than 1), for example, >2, >3, >4, >5 or more.

An exemplary array of RF energy delivery elements is illustrated in FIG. 1B. An array 5 may include a plurality of energy delivery elements 1 placed in a predetermined order, for forming elongated heated volumes 10 of the tissue when the RF generator (not illustrated) may be activated and at least one of the RF delivery elements may be in contact with the tissue. The tissue in treated volumes 10 may be heated due to the application of RF energy via energy delivery elements 1, thus firming the tissue. In some embodiments, array 5 may include a plurality of bipolar energy delivery elements each having electrode 2 and 2a (illustrated in the top first rows in FIG. 1B) and/or may include a plurality of monopolar elements 2d (illustrated in the bottom row in FIG. 1B).

As used herein all the disclosure discussing heated elongated volumes created by applying RF currents via pairs of bipolar electrodes is applicable also for elongated treated volumes created by applying RF currents via monopolar electrodes.

The treated volume shape, dimensions and depth may be affected by the RF electrodes configuration, the RF energy parameters and tissue properties, such as, heat dissipation and thermal relaxation time characteristics. For symmetric configuration of RF bipolar electrodes, the treated volume may have a symmetry line centered between the electrodes and the treated volume may be adjusted to be centered in between the electrodes or to be separated into two zones adjacent to the electrodes as will be described below.

FIGS. 2A-2B and FIGS. 3A and 3B are illustrations of some exemplary energy delivery elements according to some embodiments of the invention. In one exemplary embodiment, an RF delivery element 1 may include bipolar pair of electrodes 2 and 2a of opposite polarity or a single monopolar electrode 2d. Element 1 illustrated in FIG. 2A may include an electrode length 30 ("L") that may be significantly longer than the distance 40 ("W") between the electrodes. The volumetric tissue treated volume 10 may have elongated shape having its long axis parallel to the electrodes long axis. As illustrated in FIG. 2A and FIG. 2B, the closer the electrodes are to each other, the smaller the inter-electrode distance W is, and a higher length L to distance W ratio of treated volumes 10 may be reached. In FIG. 2B the inter-electrode distance W is larger than the distance W in FIG. 2A, while the length L is maintained, and consequently the length L to distance W ratio is lower than in FIG. 2A. According to some embodiments, the ratio L/W may be >1 (larger than 1), for example, larger than 2, 3, 4, 5 or more. Assuming the same RF frequency, the treated volumes may be shallower for closer electrodes, such as the electrodes of FIG. 2A and deeper for more distant electrodes, such as the electrodes illustrated in FIG. 2B. As the distance W between the electrodes increases, a set of RF parameters can produce two separated elongated treated volumes, each elongated treated volume close to one of the electrodes as described herein with reference to FIG. 18D.

Figure 18C:
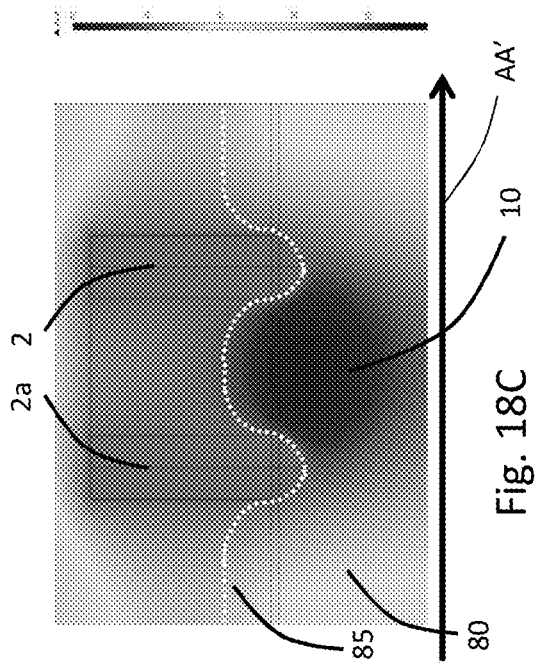
FIGS. 18B-18C are heat intensity maps of treated tissues received from a computer simulations according to some embodiments of the invention.
Figure 18D:
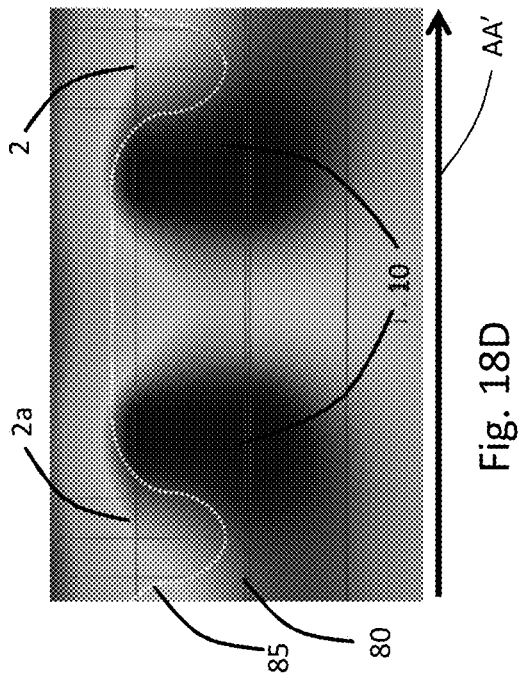
FIG. 18A is an illustration of a pair of bipolar RF electrodes according to some embodiments of the invention.
Figure 18B:
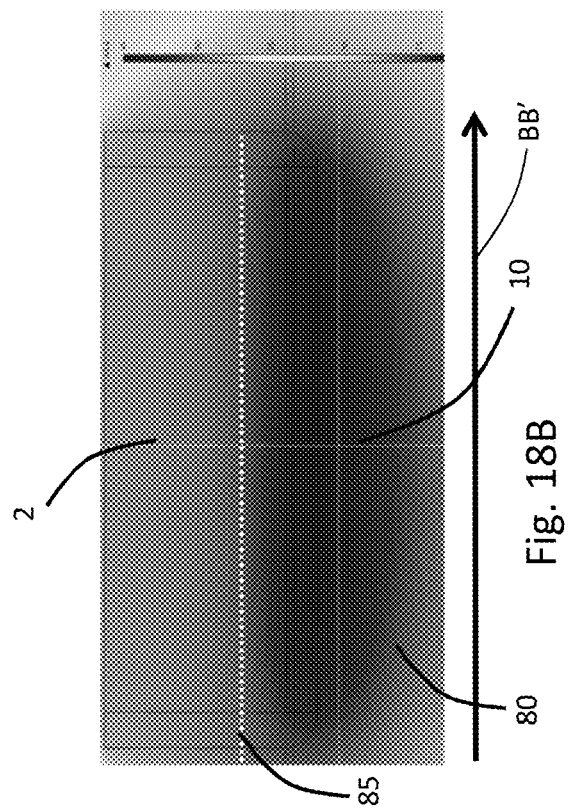
Figure 18A:
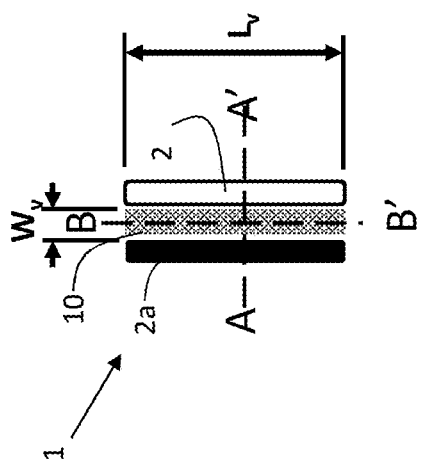

FIG. 18A is an illustration of a pair of bipolar RF electrodes 2 and 2a or a single monopolar electrode 2d that creates elongated treated volume 10. Cross section AA' may be transverse to the longitudinal dimension of electrodes 2 and 2a or a single monopolar electrode 2d and cross section BB' may be parallel to the longitudinal dimension of electrodes 2 and 2a. FIGS. 18B, 18C and 18D present simulation results of a heat impact profile in treated volume 10 of tissue 80 having exposed skin portion 85, post RF delivery between electrodes 2 and 2a or between a single monopolar electrode 2d and a current collecting electrode, according to embodiment of the invention. FIG. 18B is a view of the cross section along BB' and FIG. 18C is a view of the cross section along AA' of the heat profile of treated volume 10 in a configuration where the electrodes are in close proximity. The cross sections may describe an elongated treated volume 10 having high ratio between the orthogonal dimensions (e.g. length $L_v$ and width $W_v$) of treated volume 10. FIG. 18D presents a cross sectional view along line AA' of the heat profile of treated volume 10 for the setup described in FIG. 18a having increased distance between the electrodes 2 and 2a or increase the elongated dimension of monopolar electrode 2d and increased electrodes protrusion. As used herein electrodes protrusion is defined as the depth that electrodes 2 and 2a or a single monopolar electrode 2d are being pushed into exposed skin portion 85. Due to the larger distance between the electrodes (e.g., the distance is larger than the heat dissipation distance for a particular set of RF energy delivery parameters (power, frequency, time, etc.), in this configuration the impact may be formed as a separated two sub-volumes 10, each sub-volume 10 in relative proximity to one of electrodes 2 and 2a or a single monopolar electrode 2d.

In another exemplary embodiment, illustrated in FIGS. 3A-3B, for each RF energy delivery element 1 having bipolar pair of electrodes 2 and 2a, an electrode length L may be significantly shorter than the distance between the electrodes W. In yet another exemplary embodiment, for each RF energy delivery element 1 having a single monopolar electrode 2d, an electrode length L may be significantly shorter than the electrode width W. The treated volume 10 may have elongated shape having a longitudinal dimension parallel and substantially equal to the distance W between the electrodes. As seen in FIG. 3B, for a given electrode length L significantly shorter than the inter-electrode distance W, the larger the inter-electrode distance W is, treated volume 10 may have a more elongated shape. The ratio between electrode length L and inter-electrode distance W, L/W may be <1 (smaller than 1), <0.5, <0.33, <0.25 or less.

Referring to FIGS. 4A and 4B that are illustrations of exemplary arrays 5 of energy delivery elements (1 in FIGS. 1A, 2A, 2B. 3A and 3B) according to some embodiments of the invention. Each of RF energy delivery elements in each array 5 may be in active communication with an RF generator (not illustrated) and with a power source and a controller (also not illustrated). Arrays 5 may be designed to directionally tighten an area of tissue. In FIG. 4A arrays 5 may include RF bipolar electrode's pairs (RF energy delivery elements 1) or a plurality of monopolar electrodes 2d that may be placed over the treated area. In order to achieve directional tightening, the treated volumes 10 of each pair and their distribution over the tissue may be designed to have significant different dimension in direction 31 compared to another direction 32 both in micro level such that the distance between the electrodes $w$ is larger than the length of the electrode $\ell$ $w \gg \ell$ and as accumulated dimensions of the overall treated volumes in macro level, such that W>>L and the resulted impact may be higher along direction 31 as compared to direction 32. A similar effect may be achieved using electrode having a distance between the electrodes $w$ smaller than the length of the electrode $\ell$ so that $\ell \gg w$, as illustrated in FIG. 4B. The accumulated dimensions of the overall treated volumes in a macro level, may be such that L>>W and the resulted impact may be higher along direction 31 as compared to direction 32.

Referring to FIG. 5A an illustration of an array of RF energy delivery elements according to some embodiments of the invention and a corresponding graph showing heat contributions in the tissue are shown FIG. 5A shows an array of RF energy delivery elements configuration where a distance 17 between electrode pairs or the monopolar electrodes may be smaller than the heat dissipation distance per a treatment time period. The heat dissipation of the electrodes pairs is illustrated in graph 50 of FIG. 5A and may be a function of the electrodes and pair geometry configurations, the area or volume that is treated by applying RF energy (treated volume 10) by each pair of electrodes, the heat conduction properties of the treated tissue, and the like. Each pair of electrodes or the monopolar electrode contributes heat that dissipates mainly in the corresponding treated volume. However, some of the created heat may dissipate from the treated volumes into the volume of tissue between pairs of electrodes in an array, also referred to as distance or gap 17. The heat distribution contributed by each pair the monopolar electrode is illustrated in graph 50 of FIG. 5A. Graph 60 is an illustration of the accumulated heat distribution from all the pairs. In some embodiments, not only the treated volumes 10 between the electrodes are heated to the impact level but also the volumes of tissue in gaps 17 between heated volumes 10 are heated to the impact level due to the accumulation of dissipated heat and the consequent loss of fractional impact.

In some embodiments, when gap 17 between heated volumes 10 is larger than the heat dissipation distance per time of each heated volume 10, then the inter pairs the monopolar electrode volumes of gap 17 may not be heated to the level desired to produce impact (for example, tightening). This may enable keeping fractional directional effect and may prevent bulk heating while the combined effect may be a combination of separated treated volumes. In this case the tissue in the volume spaces of gap 17 between the treated (e.g., heated) volumes 10 may be affected not by direct heat but by other biological or physical mechanisms. An example for the effect of biological or physical mechanisms, such as tightening impact, formed by an array of parallel elongated bipolar pairs is illustrated in FIGS. 5B and 5C. Tissue 8 may be heated by an array of RF bipolar electrodes 9. Treated volumes 10 may be tightened by some percentage of their dimensions TP (Tightening Percentage) due to the derived heating.

In some embodiments, an accumulated elongated treated volume 173, illustrated in FIGS. 5B and 5C may include the sum of adjacent treated volumes 10 along a direction 73. In FIG. 5B, for each of accumulated elongated treated volume 173 the tightening of the tissue along direction 73 may be substantially equal to the tightening percentage, multiplied by the accumulated width $w$ (e.g., the distance between the electrodes) of treated volumes 10 along direction 73. The tightening of the tissue of accumulated elongated treated volume 173 in direction 75 transverse to direction 73 may be substantially equal to the tightening percentage, multiplied by the length $\ell$ of heated volumes 10 (e.g., the length of the electrodes) along direction 75. These tissue tightening values may be given by equations (1) and (2):

$$T_W = TP * \Sigma w \quad (1)$$

$$T_L = TP * \ell \quad (2)$$

In FIG. 5C for each elongated treated volume 173 the tightening of the tissue along direction 73 may be substantially equal to the tightening percentage, multiplied by the accumulated length $\ell$ of heated volumes 10 (e.g. the electrodes length) and tightening of elongated treated volume 173 in direction 75 may be substantially equal to the tightening percentage, multiplied by the width $w$. The tissue tightening values may be given by equation (3) and (4):

$$T_L = TP * \Sigma \ell \quad (3)$$

$$T_W = TP * w \quad (2)$$

Gaps 17 between heated volumes 10 that may have not been heated to a level that may cause tightening, may undergo elastic and sheer forces due to the shrinkage of adjacent treated volumes 10. These forces may pull tissue 8 in these volume gaps 17 and may cause a reduced level of tightening compared to the tightening level of treated volumes 10. The tightening of gaps 17 may be dependent on: the dimensions of treated volumes 10 (i.e., $\ell$ and $w$) and gaps 17, on the shrinkage levels of treated volumes 10 (e.g., TP), on the tissue's mechanical characteristics and/or on the temperature in the tissue between heated volumes 10 which may be dependent on the heat dissipation from treated volumes 10. Other parameters may affect the tightening effect at gaps 17. The tightening along directions 74 along gaps 17 between treated (e.g., heated) volumes 10, may be given by equation (3), for array 9 of FIG. 5B:
Tightening between treated volumes:

$$T_{74} = [TP * \Sigma w] * CTF(D, T(HD), M(T)) \quad (5)$$

where:
CTF=Tissue Coupled Tightening Factor
D=Distance between electrode lines (e.g., gap 17)
T(HD)=Tissue Temperature which is dependent on the heat dissipation
M (T)=Tissue mechanical parameters that are temperature dependent. The impact intensity and the treated volume shape, dimensions and location between the electrodes may be affected and controlled by a combination of parameters including: electrode configuration and spacing, electrode protrusion into the tissue, the tissue heated temperature profile over time, the RF current parameters, such as frequency, pulse profile, pulse modulation, intensity and duration, heat dissipation characteristics, thermal relaxation time of the particular treated tissue and cooling profile of the electrodes and the tissue surface properties.

FIGS. 6A-6B are illustrations of exemplary embodiments, in which different electrode configurations are used to set elongated volumetric treated (e.g., heated) volume 10 having distance $w$ between the electrodes and length $\ell$ of the electrodes). In FIG. 6B a set (e.g., an array) of elongated RF bipolar pairs (e.g., RF energy delivery elements 1) or monopolar elongated electrodes may be placed to form a plurality of heated volumes 10. The RF energy delivery elements are such that the longitudinal dimensions of treated volumes 10 are substantially parallel to length $\ell$ of electrode with inter RF energy delivery elements gap 17 larger than the heat dissipation distance of each delivery element. In FIG. 6A a set of shorter RF pairs or shorter monopolar electrode (e.g., RF energy delivery elements 1) with larger inter-electrode distance $w$ may be placed to form heated volumes 10 similar to those illustrated in FIG. 6B. The combined tightening at the overall treated area may be a combined effect of all elongated heated volumes 10 and may be given by Equations 6.

6) for the array of FIG. 6A $$T_L = TP * \Sigma \ell \quad (6.1)$$

$$T_W = TP * w \quad (6.2)$$

for the array of FIG. 6B $$T_L = TP * \ell \quad (6.3)$$

$$T_W = TP * \Sigma w \quad (6.4)$$

FIGS. 7A to 7D are illustrations of additional exemplary electrode configurations according to some embodiments of the invention. A set (e.g., an array) of elongated bipolar pairs or elongated monopolar electrode (e.g., RF energy delivery elements 1) are placed posterior to each other, along the same longitudinal direction. In FIGS. 7A and 7B the configuration may be set to prevent spacing between treated (e.g., heated) volumes 10. As illustrated in FIG. 7A, in some embodiments, each energy delivery element 1 may have at least one electrode 2' that is common to a proximal energy delivery element 1' to create a continuous elongated treated volume 10'. According to an embodiment, as illustrated in FIG. 7B as each energy delivery element 1 is tangent to at least one proximal energy delivery element 1 treated volumes 10 are tangent to each other, to create a continuous cumulative treated volume 10'.

As may be seen in FIGS. 7C and 7D, according to some embodiments, treated volumes 10 may be spaced apart to form gap 18 (between every two proximal RF delivery elements at the same row). According to some embodiments, gap 18 may be larger than the heat dissipation distance. The combined tightening at the overall treated area may be a combined effect of all elongated heated volumes 10 and may be given by Equations 7:

7) for the array of FIG. 7C $$T_L = TP * \ell \quad (7.1)$$

$$T_W = TP * \Sigma w \quad (7.2)$$

for the array of FIGS. 7D $$T_L = TP * \Sigma \ell \quad (7.3)$$

$$T_W = Tp * w \quad (7.4)$$

In yet another exemplary embodiment a plurality of elongated RF bipolar pairs or a plurality of monopolar electrodes (e.g., RF energy delivery elements 1) may be placed in a 2D array as illustrated in FIG. 8. In each row the elongated pairs may be placed such that an electrode 2 of element 1 is close to an electrode 2 of element 1', along the same direction, as to form gap 18 between two RF delivery elements at the same row. According to some embodiments, gap 18 may be larger than the heat dissipation distance. At least two rows may be placed parallel to each other as to form inter row distance 17. According to some embodiments, inter-row distance or gap 17 may be larger than the heat dissipation distance. Overall, the dimensions of distances 17 and 18 per this embodiment may be configured to enable discrete non-continuous fractional treated volumes 10 (i.e., as oppose to the embodiments disclosed in FIGS. 7A and 7B). Additionally, the sum of longitudinal dimension of treated volumes 10 across the rows $\Sigma \ell$ is significantly smaller than the sum of the treated dimensions along the rows $\Sigma w$ as given in Equations 8.

$$T_L = TP * \Sigma \ell \quad (8.1)$$

$$T_W = TP * \Sigma w \quad (8.2)$$

$$T_L << T_W \quad (8.3)$$

Figure 9:
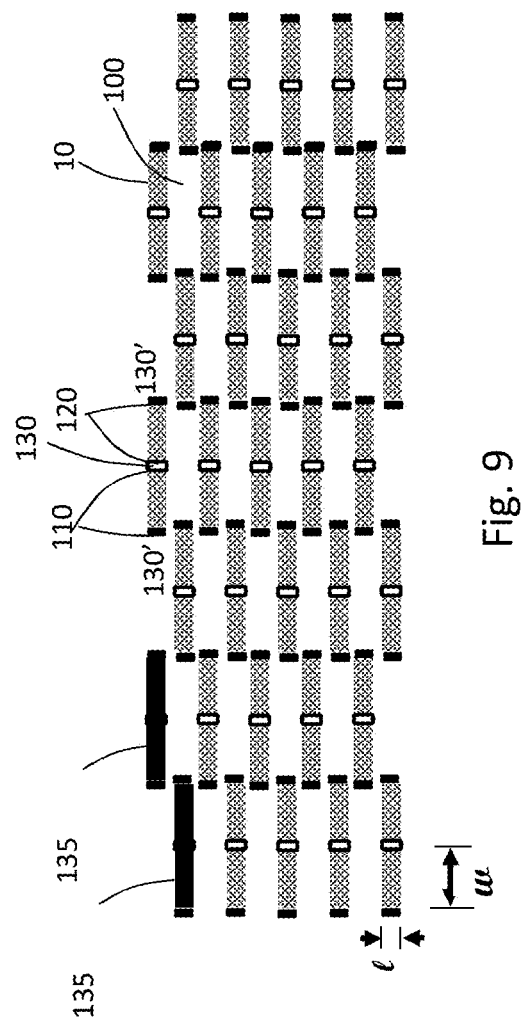
FIG. 9 is an illustration of an array of RF delivery elements according to some embodiments of the invention.

In yet another exemplary embodiment illustrated in FIG. 9, a plurality of elongated treated volume 10 formed by RF delivery elements 1 placed in a 2D array. Each two adjacent RF delivery elements 110, 120 may share one electrode having a first polarity 130 while the other electrodes 130' of elements 110 and 120 may have a second polarity opposite to the first polarity. In some embodiments, delivery elements 110, 120 may have a monopolar configuration having a plurality of elongated monopolar electrodes 135 all having the same polarity and the currents applied by these electrodes are all collected by at least one collector to "return" electrode (not illustrated). At least two rows may be placed parallel to each other but may be shifted along the rows direction in such a way that treated volumes 10 placed in a first row may be indented with respect to treated volumes 10 placed in a second row forming a volume 100 between treated volumes 10 of the other row and vice versa. The inter row distance (i.e., the width of volume 100) may be larger than the heat dissipation distance. Additionally, the sum of heated volume along the rows may be significantly larger than the sum of the heated volume across the rows as given by Equations 9.

$$T_L = TP * \Sigma \ell \quad (9.1)$$

$$T_W = TP * \Sigma w \quad (9.2)$$

$$T_L << T_W \quad (9.3)$$

In accordance with another exemplary embodiment of the current invention, illustrated in FIGS. 10A and 10B, a plurality of elongated bipolar pairs or monopolar electrodes (e.g., RF energy delivery elements 1) are placed in a 2D array. A first and second sets of elongated RF bipolar pairs may be placed such that an electrode 2 of element 1 is close to an electrode 2 of element 1', along a curved line, with inter curved line gap 17 larger than the heat dissipation distance per treatment time. At least two sets each placed in a curved line or arc may be placed such that a constant distance (gap 17) is kept along the radii of the cured lines. The first and second sets may be shifted along the curved line direction in such a way that treated volumes 10 of the first row may indented with respect to the treated volumes 10 of the second row. Inter curved-line distance 17 may be larger than the heat dissipation distance. Additionally, according to some embodiments, the sum of inter electrode distances w (as illustrated in FIG. 1A) may be much longer than the length of the electrodes L (as illustrated in FIG. 1A), in the array of FIG. 10A and vice versa in the array of FIG. 10B. This configuration may cause directional tightening along the curved lines. According to some embodiments, an array as illustrated in FIGS. 10A and 10B may be adapted to provide directional tightening along a curved line, for example, for treating anatomies like periorbital crow-feet wrinkles and the like.

Another exemplary embodiment is shown in FIGS. 11A-11B. A plurality of RF energy delivery element (e.g., a bipolar set of electrodes) illustrated in FIG. 11A are placed in a 2D array illustrated in FIG. 11B. The volumetric impact created by each electrode's pair has substantially same dimensions in so dimensions L and W are substantially equal. The density of pairs (also referred to as the spacing between pairs) along a first direction 31 is higher than the density of pairs in the second direction 32 (orthogonal to direction 31) such that the spacing between the pairs are shorter. The density may be defined as the number of RF delivery elements located at a specific area (within the array). This may result in a difference in the sum of length of treated volumes per area along direction 31 compared to the sum of length of treated volumes per area along the orthogonal direction 32. Therefore, directional impact, for instance directional tightening, may be produced along direction 31. Directional impacts according to some embodiments of the invention may form when the elongated treated volumes (or the elongated accumulated treated volume) may cause substantially different amount of tightening of the tissue in the longitudinal and transverse dimensions of the treated volumes. Accordingly, the amount tightening of the tissue in the longitudinal dimension may be substantially higher (e.g., at least 2 time higher) than the amount of tightening in the transvers dimension, causing a directional tightening or a directional impact.

Figure 12C:
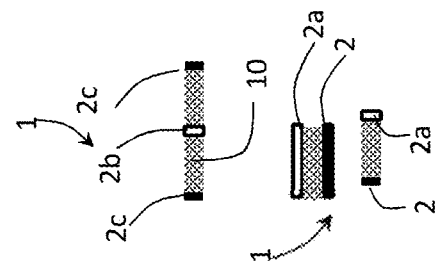
FIG. 12C is an illustration of a directional RF bipolar pair and dual RF bipolar pairs according to some embodiments of the invention.
Figure 12B:
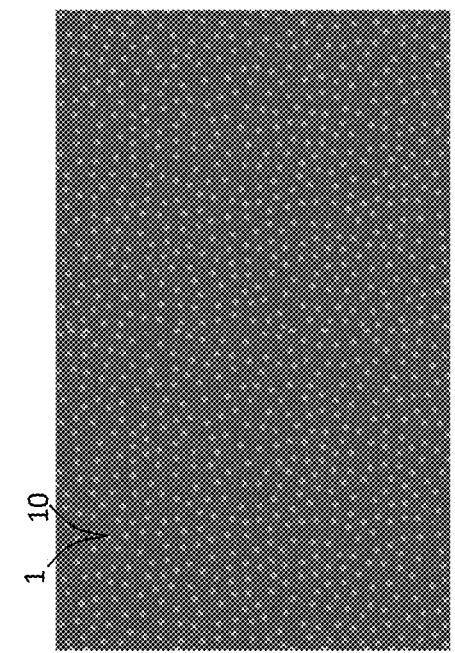
FIGS. 12A and 12B are illustrations of large arrays of RF energy delivery elements according to some embodiments of the invention.
Figure 12A:
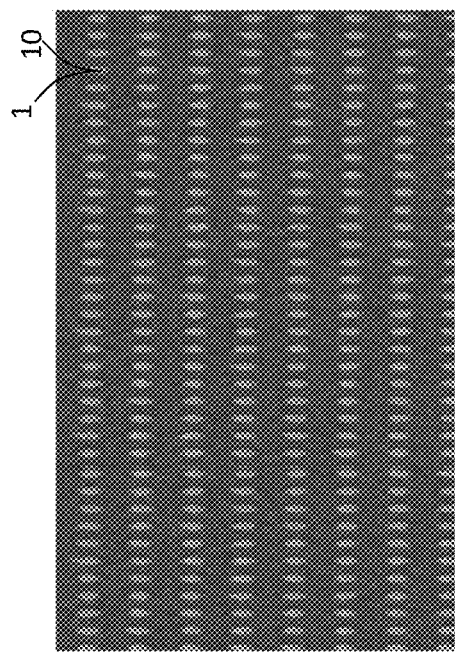

In some embodiments, method and device of the invention may be configured to enable homogeneous directional impact per accumulated affected zone. In accordance with exemplary embodiments of the current invention, electrode pairs (RF delivery elements) may be homogeneously spread in the electrodes array (e.g., patch) placed over a treated area. FIGS. 12A and 12B are illustrations of arrays of RF energy delivery elements (having a plurality of pairs of bipolar electrodes or a plurality of monopolar electrodes). Each point in the drawings represents an RF delivery element 1 that includes bipolar electrodes 2 and 2a a monopolar electrode 2d, or dual bipolar electrodes 2b and 2c and treated volume 10 as illustrated in FIG. 12C. Such homogeneous spreading, may include fixed electrode pairs density, inter-electrode distance, and inter-pairs distance that may be kept essentially constant in the entire treatment (e.g., tightening) process as illustrated in FIG. 12A. According to some embodiments, as illustrated in FIG. 12B, the RF elements may be randomly placed to form randomly located elongated directional impacts. Each point in FIG. 12B represents a directional RF bipolar pair, a monopolar elongated electrode or dual RF bipolar pairs as illustrated in FIG. 12C. All the elongated directional RF pairs may be oriented to the same direction. Homogeneous directional impact may be applied, for example, for forehead skin tightening.

In some embodiments, method and device of the invention may be configured to produce directional, degraded impact having variable impact intensity along at least one predefined direction. In some embodiments, the density of the RF delivery elements may vary within the array. In some embodiments, the array may comprise at least a first group of RF energy delivery elements located at a first area and a second group of RF delivery elements located at a second area different from the first such that a density of the RF energy delivery elements in the first area may be different from a density of the RF energy delivery elements in the second area.

In some embodiments, a distance between two neighboring RF delivery elements in any direction (e.g., inside the rows or between the rows) may be changed along a desired direction, forming a changing density of the RF delivery elements. For example, a first distance between first and second RF delivery elements may be different from a second distance between the second and third RF delivery elements, in the array of RF delivery elements. In some embodiments, the first distance may be larger than the second distance and the second distance may be larger than a third distance between the third and a forth RF delivery elements, as to form a degrading heating effect. Such an exemplary arrangement is illustrated in FIG. 13A.

Figure 13A:
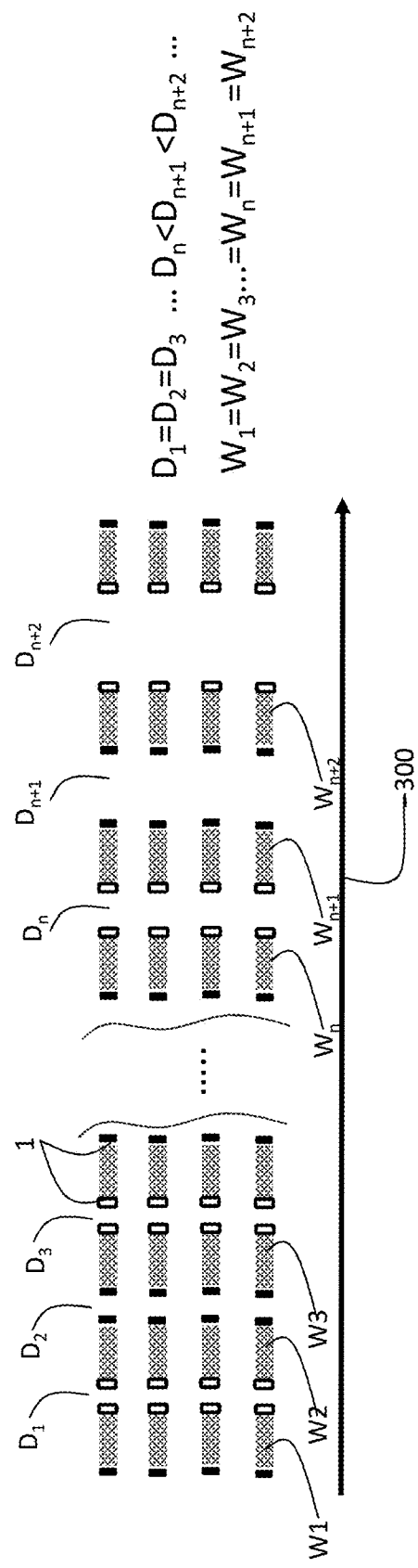
FIGS. 13A and 13B are an illustrations of arrays of RF delivery elements according to some embodiments of the invention.

Referring to FIG. 13A, that is an illustration of an array of RF bipolar pairs or an array of monopolar electrodes (e.g., RF energy delivery elements) all having same inter-electrode spacing W or width W, may be arranged in columns, the columns may substantially be equally spaced. In some embodiments, the columns spacing D may start to increase along direction 300, such that consequently the level of impact may gradually decrease. As can be seen in FIG. 13A, according to some embodiments $D_1 < D_n < D_{n+1}$ however, $W_1 = W_n = W_{n+1}$.

Figure 13B:
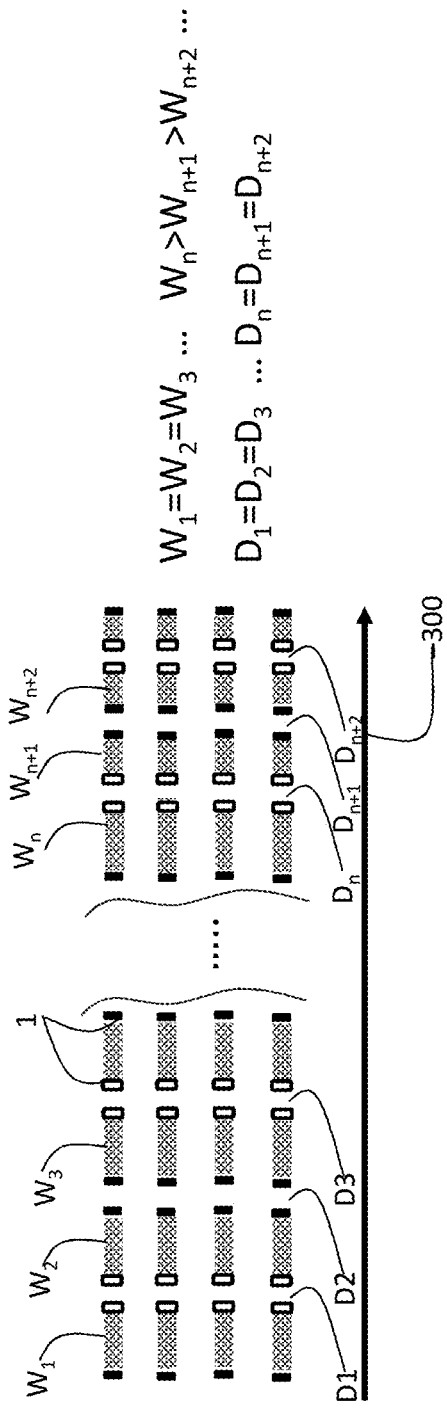

In some embodiments, the same effect may be received by changing the inter-electrode spacing W or the length W of the monopolar electrode. In some embodiments, a first distance between the electrodes in a first pair may be different from a second distance between the electrodes in a second pair. In some embodiments, the first distance between the electrodes in the first pair may be smaller than the second distance between the electrodes in the second pair and the second distance between the electrodes in the second pair may be smaller than a third distance between the electrodes in a third pair. Referring to FIG. 13B illustrating another exemplary array of RF elements (e.g., bipolar pairs or monopolar electrodes) in which the impact degradation may be produced by degraded inter-coupled electrode distance W of the pairs along a desired direction to produce gradually shallower heating effect while keeping the inter-pair distance D equal. As seen in FIG. 13B, according to some embodiments, the distance $W_1 > W_n > W_{n+1}$ while $D_1 = D_n = D_{n+1}$. The two described approaches of FIG. 13A and FIG. 13B can be combined for a specific need. In some embodiments, degraded impact may be desired and applied, for example, for treatment of the nasolabial fold, where higher tightening impact is needed in close proximity to the fold, and lower tightening intensity, of same direction is needed, the closer we get to the ear.

Figure 14:
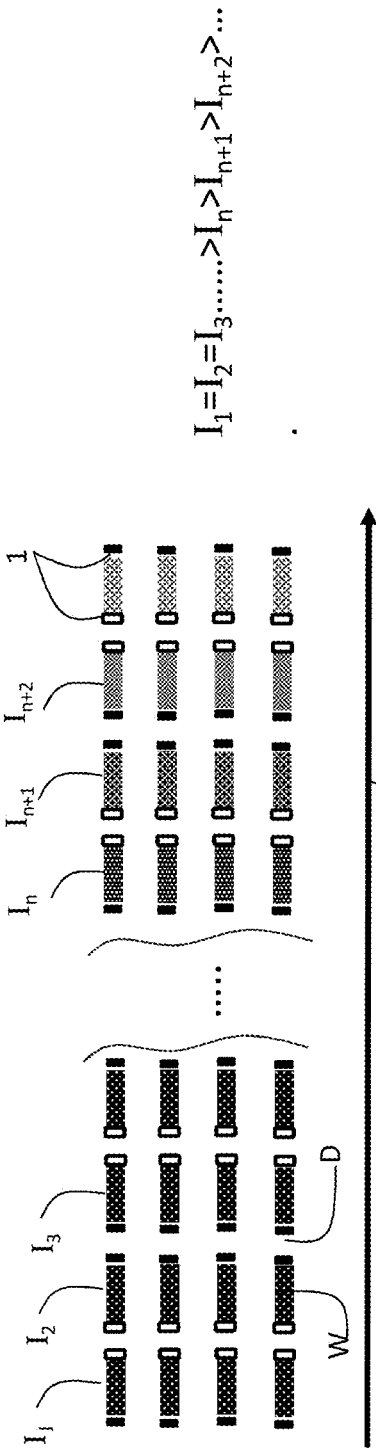
FIG. 14 is an illustration of an array of RF delivery elements according to some embodiments of the invention.

In some embodiments, a single array of RF delivery elements configuration may support both homogeneous directional impact and nonhomogeneous degraded impact, using different RF parameters for different electrode pairs or different monopolar electrodes in the array. For homogeneous effect, the RF parameters may be defined per pair or monopolar electrode to compensate for lack of homogeneity of the electrode configuration so to adjust tissue impact per predetermined zone for homogeneity purposes. Similarly, tuning of the RF parameters per pair or monopolar electrode may be used to produce nonhomogeneous effect, for example, by increasing or reducing RF parameters along a predetermined direction to produce gradual impact, as illustrated in FIG. 14. FIG. 14 is an illustration of an exemplary array of RF delivery elements according to some embodiments of the invention. In the array of RF bipolar pairs or monopolar electrodes of FIG. 14 both the inter electrode spacing W or length of the monopolar electrode and the inter pairs spacing D may be substantially equal between all the pairs. For some of the pairs or monopolar electrodes the RF parameters are equal to produce equal directional impact $I_1$ while at some point the RF parameters may be changed to produce gradually decreased Impact $I_2(x)$ along direction 300. The decreased impact may be related, for example, to reduce coagulation level, or for producing lower phenotype yielded impact, for example, stimulation instead of coagulation along predetermined direction(s). It should be appreciated that gradually increased impact may be achieved in a similar manner.

In some embodiments, similar effects may also be established by alteration of treatment regime, including number of treatments and inter-treatment intervals, per treated zones and subzones. The final desired directional impact may be established by any combination of the above and may be controlled by a controller of the system based on anatomy and tissue characteristics like thickness, degree of ptosis, local impedance and the like.

FIG. 15 is an illustration of a schematic operation method of an array of RF delivery elements according to some embodiments of the invention. Array 140 comprising a plurality of RF delivery elements may be operated such that only a sub-set 150 of the plurality of elements in array 140 is operated at the same time while all other RF delivery elements do not deliver RF energy. Array 140 may be divided into several (e.g., 4, 6, 8 or any other number of subsets) subsets of the bipolar pairs or monopolar electrodes. The sub-sets may be operated sequentially (in FIG. 15 the currently operating elements in each array are illustrated as black short lines in comparison to the grey lines that represent non-operating RF elements), with or without time delay. Since only subset 150 of array 140 is being operated per given time period, only a portion of the tissue that is in contact with activated sub-set 150 is being fractionally heated each time as illustrated in FIGS. 15 A-F. This may result in reduced heat sensation, enhanced convenience and compliance of the user. Additionally this mode of operation may require lower power source, as compared to concomitant activation of the entire array 140, and thus may be appropriate for home care treatments. The operated subset may include any number of pairs or monopolar electrodes (RF delivery elements 1), adjacent, separated or randomly selected, and the operation sequence of the subsets can be of any spatial and time sequence as desired by the treatment protocol.

As used herein, a treatment protocol may include selected parameters for the operation of an apparatus for non-invasive directional tissue treatment for a specific treatment. The protocol may include RF delivery parameters such as the RF frequency and the RF power in which the RF energy is to be delivered in the specific treatment. The protocol may further include the timing and the duration (e.g., pulses, continuous, etc.) in which the RF energy is to be delivered and the number and location of the RF delivery element (e.g., a sub-set from the plurality of RF delivery element) to which the RF energy is to be delivered. The treatment protocol may be determined by a user (e.g., a professional), by the apparatus (e.g., based on parameters of the patient uploaded into a controller associated with the apparatus) or a combination of both.

The protocol may include online monitoring and feedback of the actual treatment. This may be conducted using assisting agents, such as smartphone, and dedicated software application to control the entire procedure. Post medical evaluation to ensure applicability, there may be determination of a size of the tissue or organ to be treated and required tightening level to confirm the suitability for the procedure. Thereafter, the skin (dermis and fascia) thickness may be determined using an apparatus according to an embodiment of the invention. With the additional skin thickness data measured with the apparatus, the treatment protocol and treatment parameters per area may be defined. An exemplary protocol may include three levels: I) a determination of RF parameters for a single delivery of RF energy to a specific area (e.g., RF power, pulse sequencing, direction, depth, number of RF cycles to enable comfort use), II) a session procedure (for instance, an amount of energy that may be delivered to achieve a desired impact per day, sequencing between areas etc.), and III) an overall cycle of treatment sessions (for instance, a number of overall treatments, their daily timing, or the like). This may differ in some terms between a stationary and a moving applicator (illustrated in FIGS. 22 and 25).

In some embodiments, during an actual treatment, the apparatus (e.g., apparatus 70, 200 or 250) may be configured to detect the skin thickness and its initial temperature. Post ensuring conductivity by test pulses, system may be activated to deliver fractional treatment RF energy to a predetermined depth, using appropriate RF parameters. Temperature may be continuously measured (e.g., by temperature sensors and/or by low level tissue impedance sensing pulses) and used as control feedback for controlling the RF energy delivery parameters of the apparatus. At each treatment end the skin thickness may also be determined.

In one embodiment, the treatment results at end of treatment, as well as just before the next treatment may be used to adjust the treatment protocol, in case the improvement achieved is not as plan. According to non-limiting embodiment this may be conducted using the smartphone application. The latter may also be used to schedule and alert treatments as well as for post treatment cycle maintenance session for maintaining the results of the treatment sessions.

In accordance with another exemplary embodiment the RF electrodes' shape may be designed to reduce the RF current density at the electrode's surface which is directed towards the other electrode in a pair of electrodes (for example, the pair in RF delivery element 1 illustrated in FIG. 1A). The reduction of the current density may assist preventing overheating and hotspots at the treated tissue adjacent to the electrodes and may further reduce and even eliminate the need for tissue surface cooling. The electrodes may have rectangular rounded corner shape and a sub mm or mm thickness that may be pushed, during treatment, towards and deform the skin surface with its rounded corners and facets. Such an exemplary electrode shape is illustrated in FIGS. 16A and 16B which show a perspective view and top view (respectively) of an electrode according to one embodiment of the present invention. In accordance with yet another exemplary embodiment of the invention RF delivery parameters, such as frequency, pulse mode, modulation if pulsed, intensity and duration may be determined to form volumetric effect that takes into account the heat dissipation characteristics of the particular treated tissue to maintain the fractional nature of tissue impact and the overall elongated profile of the effect. The heat dissipation characteristics, the electrodes dissipation characteristics and the combination with RF current modulation and other RF parameters may be used for dissipating the heat at the electrodes contact area with the skin. Dissipating the heat may eliminate hot spot and may control the dissipation of heat outside of the treated area as to maintain elongated impact. According to some embodiments, other element, such as, cooling elements (not shown) may be used to assist in maintaining the volumetric elongated impact.

Referring to FIG. 17A, an apparatus for non-invasive directional tissue treatment according to some embodiments of the invention is shown. An apparatus 70 may include an array 205 of RF delivery elements 210. Array 205 may be any array of RF delivery elements according to any embodiment of the invention. When array 205 include monopolar electrodes apparatus 70 may further include a grounding or return (current collector) pad or electrodes 240. In some embodiments, grounding or return pad or electrodes 240 may be included in array 205.

Apparatus 70 may further include a radiofrequency (RF) generator 310, a power source 320 and a controller 360. In some embodiments, controller 360 may be in active communication with an image processing device 350 and an imager 355. Imager 355 may be any device for capturing images of tissues known in the art. Imager 355 may be a camera, an ultrasound device, a CT device, an X-ray device, MRI device or the like. In some embodiments, apparatus 70 may further include one or more sensors 230, and controller 360 may include a timer and a time control unit configured to automatically monitor and control employment of the apparatus (e.g., timing and duration of the heat treatment).

Array 205 may include a plurality of RF delivery elements 210 such that each of the RF energy delivery elements may include a pair of electrodes (e.g., electrodes 2, 2a, 2b or 2c illustrated in FIGS. 1-3 and 12C) with opposite polarity or monopolar electrodes 2d illustrated in FIG. 1B as disclosed herein. Each electrode in element 210 may have a first dimension and a second dimension, the first dimension perpendicular to the second dimension and to an imaginary line connecting the pair of electrodes to each other. Furthermore, the first dimension of each electrode (either bipolar or monopolar) (e.g., L illustrated in FIGS. 1-3) in element 210 and the distance between the electrodes (e.g., W illustrated in FIGS. 1-3) in each pair may be configured to create an elongated treated volume of tissue (e.g., volume 10 illustrated in FIGS. 1-3) when RF generator 310 may be activated and at least one of the RF delivery elements may be in contact with the tissue. Apparatus 70 may further include a cooling unit (not illustrated) to reduce the electrodes and/or the treated tissue temperature.

Apparatus 70 may further include at least one temperature sensor 230, an RFID sensor 220, or any other suitable sensor that may be monitored by controller 360 to control the RF parameters applied to array 205. In some embodiments, array 205 may be included in a consumable or disposable patch. Additional sensing and controlling may be done based on sensing the tissue impedance by applying low current (e.g., monitoring current) via element 210 or by a specific sensor to monitor the tissue temperature and to use these measurements to assess the amount of RF energy (and RF parameters) required for achieving a level of impact (e.g., directional tightening) of the treated tissue.

According to some embodiments, a flexible plate (e.g. a patch) may include an electrode array (an array of RF delivery elements) that may be: embedded in an attachable flexible plate; 3D printed into an attachable flexible plate, or may be an integral part of tissue attachable flexible plate. The flexible plate may be designed to have dielectric characteristics that differ from the conductivity characteristics of the electrodes. The flexible plate may also be configured to easily and comfortably be placed, fit and/or attached to anatomies of different morphologies. It may be formed of flexible dielectric materials such as silicone, silicone gel, fabric, flexible printed circuit board and any other form or material known in the art. The flexible plate may be covered with adhesive layer for good adherence to the skin, as well as for enhanced electrical coupling of the electrical current between the electrodes and the affected skin. The adhesive layer may for instance be in form of gel, glue or double sided adhesive sheet and may be an integral part of the flexible plate (also referred to as flex), or placed over flex or over skin before treatment.

According to some embodiments, RF generator 310 may be configured to supply RF energy to RF delivery elements at various RF delivery parameters. The RF delivery parameters may include, the RF frequency(ies), RF power levels, or the like. For example, the RF energy generated by the RF generator may be in the range of 50 kHz-10 MHz or in the range of 500 kHz-3 MHz. In some embodiments, the power supplied by power source 320 may be in the range of 1-100 Watt.

Other RF energy delivery parameters may include: timing of the RF energy application, the duration of the RF energy application and a selection of a sub-set of RF energy delivery elements from the plurality of elements in the array for delivering the RF energy to the tissue and a particular timing of the delivery. In some embodiments. RF generator 310 may be configured to generate pulses of RF energy according to instructions received from controller 360, based on a treatment protocol. For example, each RF pulse' duration may last between 50 milliseconds and 60 seconds.

In accordance with yet another exemplary embodiment of the current invention, apparatus 70 may further include the use of imaging diagnostic and feedback tool in conducting the directional impact such as directional tightening. The imaging diagnostic tool may be conducted using 2D or 3D pictures, received from any known capturing device (e.g., imager 355), and image processing unit 350 as shown in FIG. 17A.

In some embodiments, controller 360 may be configured to cause the delivery of RF energy by the RF delivery elements (e.g., element 1 illustrated in FIGS. 1-12, 210, etc.) at predetermined RF parameters to create the elongated heated volume (e.g., volume 10). Controller 360 may include any processing unit and storing device that is configured to store and execute instructions according to any embodiment of the invention. For example, the processing unit may include a central processing unit (CPU), a chip or any suitable computing or computational device. Controller 360 may also control the cooling unit (not illustrated).

Figure 17B:
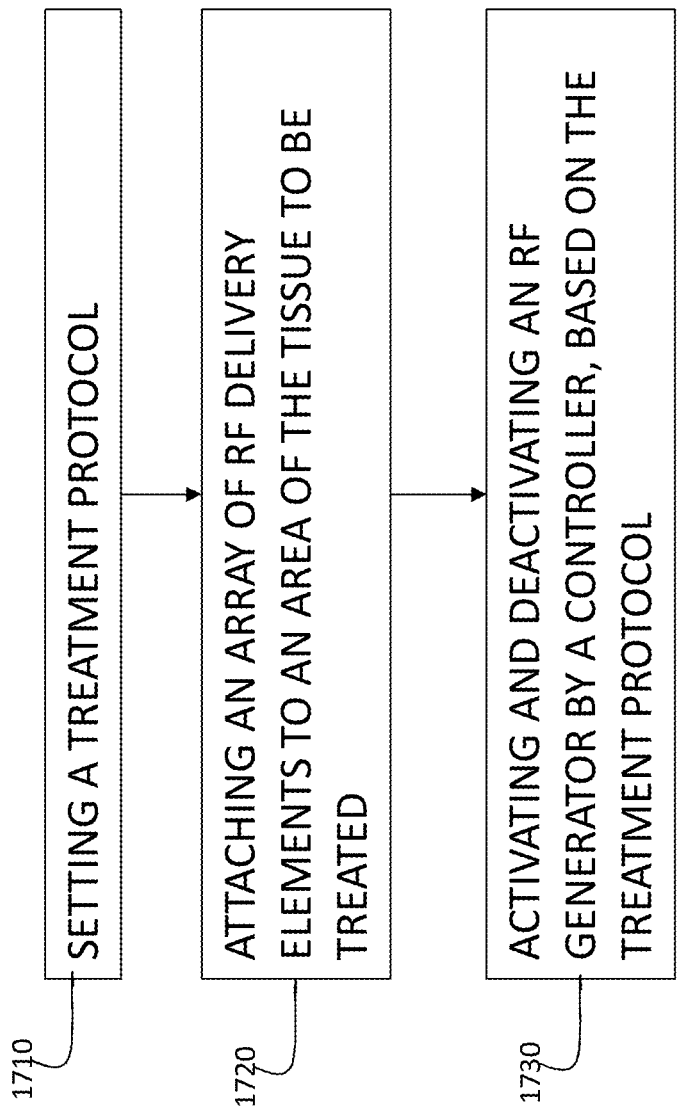
FIG. 17B is a flowchart of a method of non-invasive directional tissue treatment according to some embodiments of the invention.

Reference is now made to FIG. 17B which is a flowchart of a method of non-invasive directional tissue treatment according to some embodiments of the invention. The treatment may be performed by any apparatus according to embodiments of the invention, for example, apparatus 70. In box 1710 the method may include setting a treatment protocol. The treatment protocol may include selecting the RF delivery parameters (e.g., current levels, plus duration, plus timing or the like), selecting a patch containing an array of RF delivery elements (e.g., array 205) and/or selecting a sub-set of RF delivery elements (e.g., sub set 150) to be operated and the timing for operating the sub-set.

In some embodiments, setting of a treatment protocol may include capturing, by imager 355 (e.g., a capturing device), at least one image of the area of the tissue to be treated and analyzing the at least one image, by the image processing unit (e.g., image processing unit 350), to determine the required treatment. The method may include capturing an image (e.g., by imager 355) of the treatment zone and processing the image (e.g., by image processing unit 350 and controller 360) for receiving comprehensive 2D or 3D model. The method may further include conducting picture analysis and measuring tissue characteristics, either by measuring direct impedance of the tissue using the array or by other sensors (e.g., temperature sensors). The tissue characteristics may include at least one of: tissue type, tissue thickness, tissue temperature, and tissue impedance. The analyzed image(s) and measured characteristics may be used for determining treatment protocol according to the required treatment.

For example, the image analysis and measured characteristics may be used for determination of lesion or ptosis level, for determination of suitability of the process, for selecting directional treatment and analyzing expected results. The outcome of this process may include image based recommendation for the flexible plate or patch design and size and placement orientation of the array and determination of RF treatment parameters. The analysis may further predict an expected number of sessions and treatment algorithms per session and for the entire treatment. The analysis may be used in follow up process and to update the treatment parameters if needed. After the treatment the imaging analysis may be used to determine the overall impact.

An exemplary optical imaging diagnosis and feedback may be used for breast ptosis or pseudoptosis using directional volumetric tightening impact. It may similarly be used for facial wrinkles or folds diagnosis and feedback, for underarm laxity treatment and the like. The directional tightening may include further diagnostic tools such as impedance monitoring to determine tissue temperature or tissue type and thickness.

In box 1720, the method may include attaching at least a portion of an array of RF delivery elements, powered by an RF generator (e.g., generator 310), to an area of the tissue to be treated. For example, a patch having a form of a bra (as illustrated and discussed with respect to FIG. 25) may be placed on a patient's chest for treating breast ptosis. Alternatively, a randomly arranged array of elements, as illustrated in FIG. 12B, may be placed on the forehead of a patient for wrinkle removal. Other shapes and types of patches, flexible plates and applicators may be used according to, for example, the required treatment and the requirements of the patient.

In some embodiments, after attaching at least a portion of an array of RF delivery elements, the setting or determining the treatment protocol may further include: applying one or more pluses of RF energy, at level of RF energy lower than the RF energy required to physiologically affect the treated volume, and measuring impedance received at the one or more pulses. Based on the measured impedance, the controller (e.g., controller 360) may be configured to determine tissue characteristics, such as, tissue type, tissue thickness and tissue temperature, and determine treatment protocol based the tissue characteristics. In some embodiments, the method may include setting the treatment protocol based on information received from an imager (e.g., captured images) and measured tissue impedance. Controller 360 may be configured to process and analyze the image data received from the imager and tissue impedance measurements received from the RF generator to set the treatment protocol. In some embodiments, the method may include re-measuring the impedance at at least one of: during the treatment and at the end of the treatment.

In box 1730, the method may include activating the RF generator and deactivating the RF generator by a controller (e.g., controller 360), based on the treatment protocol. For example, controller 360 may activate only a sub-set of RF delivery elements at a selected timing and/or apply different RF energy levels to different RF delivery elements in the array or the sub-set of elements.

In some embodiments, the method may include selecting, by the controller (controller 360), two or more sub-groups of RF delivery elements from the array of RF delivery elements. In some embodiments, the method may include applying a first set of RF delivery parameters to a first group of RF delivery elements and applying a second set of RF delivery parameters to a second group of RF delivery elements, wherein the first set is different from the second set, wherein the first set is different from the second set. In some embodiments, such method of applying the RF energy may allow forming a decreased (or increased) amount of heating along a certain direction, as illustrated and discussed with respect to FIG. 14. In some embodiments, such method may include applying a third set of RF delivery parameters to a third group of RF delivery elements, wherein the heat per unit volume delivered when applying the second set of RF delivery parameters may be lower than the heat per unit volume delivered by applying to element 1 the first set of RF delivery parameters and the heat per unit volume delivered by applying the third set of RF delivery parameters may be lower than the heat per unit volume delivered by applying the second set of RF delivery parameters.

In some embodiments, the method may further include re-measuring tissue characteristics at at least one of: during the treatment and the end of the treatment cycle and/or recapturing, by an imager, at least one image of the area of the treated tissue at at least one of: during the treatment and the end of the treatment.

In yet another exemplary embodiment of the current method and apparatus, the apparatus may also be designed to stimulate collagenesis, coagulate collagen and tighten skin in areas such as, but not limited to, face for face lifting, wrinkles or folds reduction and skin rejuvenation, loosen underarm for its tightening, and to breast area for breast remodeling.

In still another exemplary embodiment of the current method and apparatus, the apparatus may apply non-invasive types of cosmetic treatment to the body including combination of forms of energy such as, but not limited to RF energy combined with light (e.g., infra-red or visual light) energy. Other modalities such as cooling elements may also be integrated thereto.

In another exemplary embodiment of the current method and apparatus the tissue attachable patch/flexible plate may be supplied by a rechargeable and/or disposable power and RF source.

Figure 19:
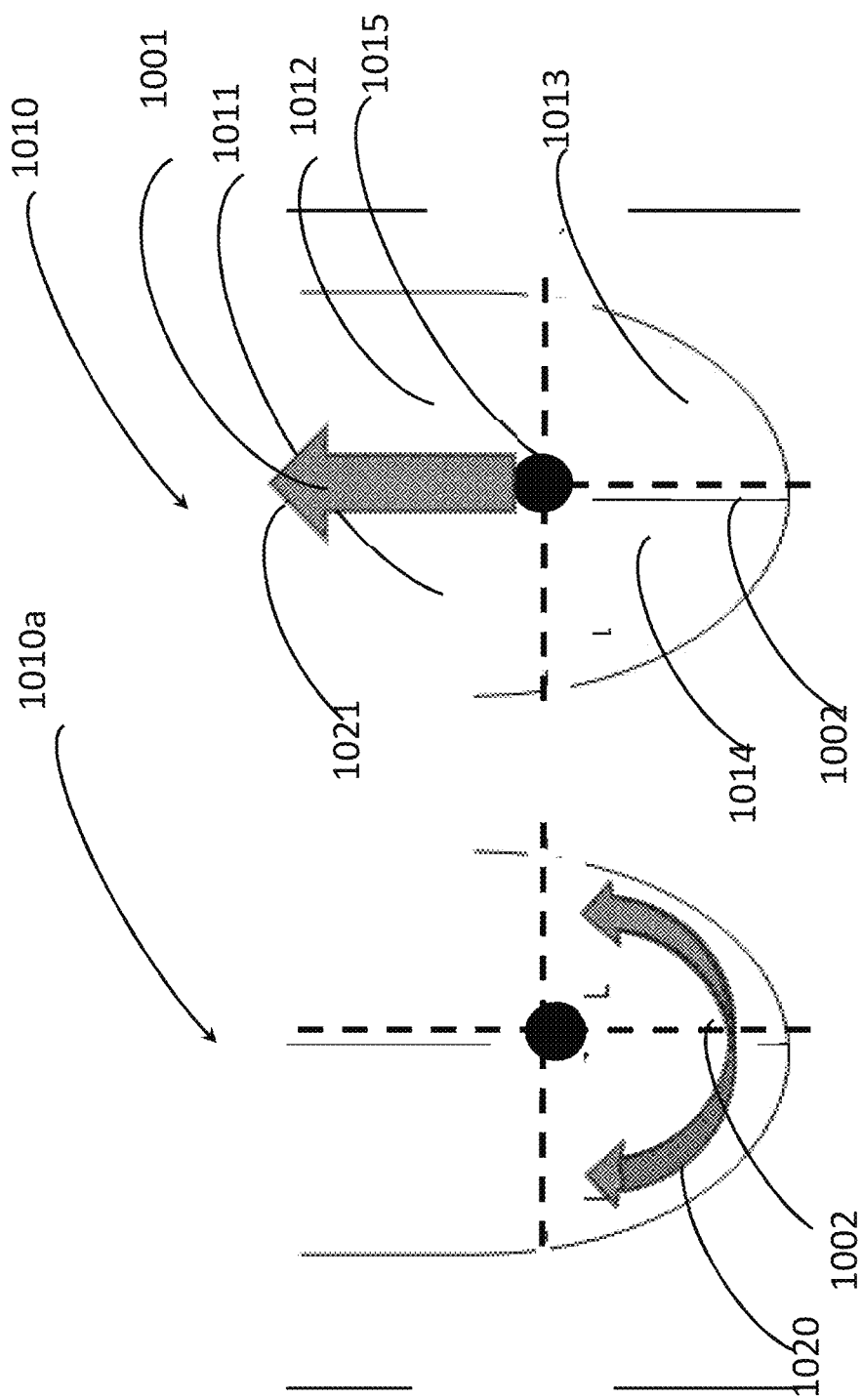
FIG. 19 is an illustration of desired tightening directions per breast poles according to embodiments of the present invention.

Reference is now made to FIG. 19 which is an illustration of breasts and desired impact of tightening and collagen synthesis per breast quarters according to some embodiments of the invention. Breasts 1010 and 1010*a* may each be schematically divided into four quarters: upper inner quarter 1011, upper outer quarter 1012, that forms together upper anatomical pole 1001, lower inner quarter 1014 and lower outer quarter 1013, that forms together lower anatomical pole 1002, with respect to breast nipple 1015. During mastopexy procedure, excess skin may be removed between lower inner 1014 and lower outer 1013 quarters of each breast 1010 and 1010*a*. Post suturing, this superficial tissue reduction may be equivalent to shrinkage along axis 1020. This may further result in upwards push of the tissue of the lower and upper breast quarters in direction of axis 1021, which may be equivalent to impact caused by shrinkage or tightening of tissue along axes 1020 and 1021.

FIG. 20 is a schematic illustration of RF delivery elements array according to some embodiments of the invention for desired direction of impact for the upper and the lower breast 1010 and 1010*a* poles 1002. RF delivery elements 150 of the army 1050 to treat the lower breast poles are oriented to cause tightening along direction of axis 1020 and the RF delivery elements 150 of the array 1051 to treat the upper breast poles are oriented to cause tightening along direction of axis 1021.

Reference is made to FIGS. 21A and 21B which are schematic illustrations of electrode arrays and wiring for achieving a non-continuous tightening impact. This intends to prevent a linearly continuous tightening or stimulation impact on breast surface that may result in linear skin patches at the phenotype level. FIG. 21A illustrates a mechanism to disrupt such linear effect while the electrodes of the positive 1068 and the negative 1069 electrical branches may not be in a linear continuous design. Positively charged electrodes 1060, 1060*a*, and 1060*b*, may electrically communicate with negatively charged electrodes 1061 and 1061*a*. Negative electrodes 1061, 1061*a* may not be positioned in linear design with positive electrodes 1060, 1060*a* and 1060*b* but may be shifted aside. Electrical paths formed 1062, 1062*a* and their derived heating impact may be diagonal, distorting and even preventing the linear impact at phenotype level. FIG. 21B describes another non-limiting embodiment for preventing a linear patching. A linear patching, according to some embodiments of the invention may include a situation where at the phenotype level lines of treated volumes are seen on the surface of the skin, following a treatment (e.g., heating) of the tissue In some embodiments, linear patching appearance may be blurred out by breaking the linearity or by breaking the continuity of a long linear impacted zone.

According to some embodiments, several current loops may be formed and may be used alternatively for at least one of RF branches 1077-1079 and electrodes array 1077*a*-1079*a* related to RF branches 1077-1079. In this non-limiting embodiment, there may be a single negatively charged branch 1079 and two positively charged branches 1077, 1078 that may be alternatively connected. For a given treatment, negatively charged electrode 1079*a* of branch 1079, may be electrically connected with either electrode 1077*a* of positively charged branch 1077, or with electrode 1078*a* of positively charged branch 1078. Accordingly, electrical path and the electrical path impact in the tissue may be path 797 for a certain treatment when branch 1077 is connected, or path 798 for a given treatment when branch 1078 is connected, for instance during another (e.g. consecutive) treatment session when path 797 has already healed.

Figure 22A:
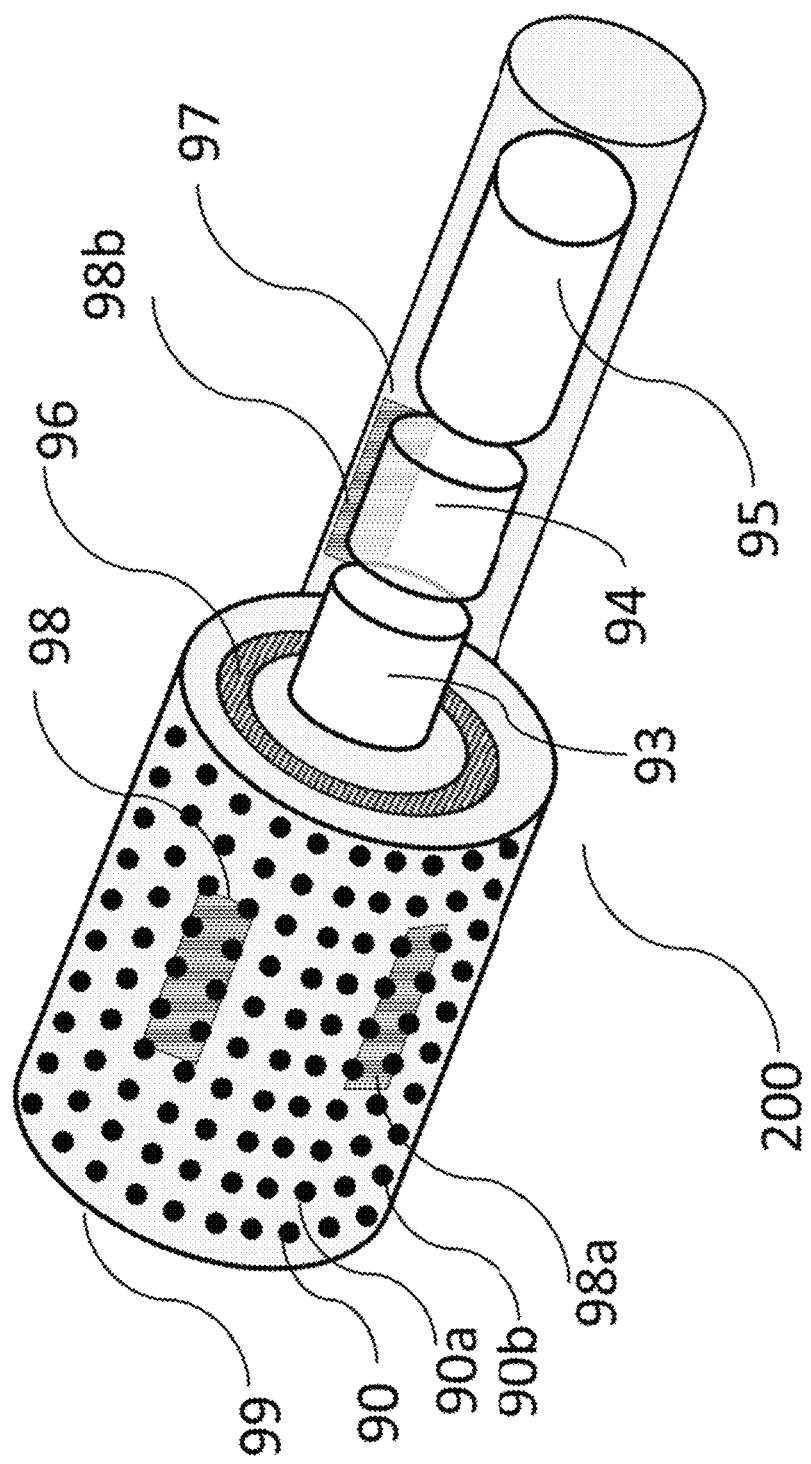
FIGS. 22A and 22B are illustrations of moving applicators for achieving desired impact in treatment in motion according to some embodiments of the invention.

FIG. 22A is an illustration of a moving applicator for achieving desired impact of breast lifting (or any other tissue treatment) using treatment in motion. Applicator 200 may include a grip 97 and cylindrically shaped treatment roller portion 99. The treatment portion 99 may include an electrically isolated non-conductive material, having an array of electrodes 90, 90a, 90b (each pair of negatively charged electrodes or monopolar electrodes may be included in a single RF delivery element). In one embodiment the array of electrodes may be embedded within the roller's surface, whereas the inter-electrode wiring is in the inner part (not seen) of the roller. In another embodiment a sheath with printed electrodes or flexible printed circuit board with printed electrodes may be attached or stick to the roller surface as a replaceable or disposable unit. Such a replaceable or disposable electrode unit may enable the use of different electrodes configurations (e.g., different RF delivery elements as disclosed herein with respect to FIGS. 1-16), and spacing to be adapted to various treatment parameters, for example, tissue thickness (different inter-electrode spacing) and treatment direction. Replaceable electrodes unit may have another advantage of sterilization. The replaceable unit may be cleaned and sterilized, may be replaced for another patient use, or may be replaced when it becomes worn.

Each electrode pair or each monopolar electrode (e.g., RF delivery elements) or sub set of electrode pairs or a sub set of monopolar electrodes may be activated at a specific polarity at any instantaneous time to follow a desired heat impact direction and depth per breast condition, breast upper or lower quarters, and according to a specific treatment protocol. The hand piece may be equipped with at least one orientation sensor 98 that indicates its upward or downward facing. This sensor may be embedded in the roller inner surface. In some embodiments, more than one sensor 98 and/or 98a may be provided for example, at orthogonal positions to ascertain the roller's angular orientation. Alternatively, rotation or angular encoder 96 may be used instead of one or two of the orientation sensors, or in addition to it. In another configuration the orientation sensor may be attached to the hand-piece non-rotating component 98b. The grip may contain RF driver 93, system controller 94 and power supply or batteries 95. To ensure that every treated area may receive the desired energy planned to achieve the desired tissue heat profile, the device may include a motion sensor 96 and a speed detector together with encoder. This assembly may enable RF pulses delivery per speed of movement. The device may also include surface cooler to ensure comfort use. The cooler may be in form of Thermo-Electric-Chiller or air cooling element.

Figure 22C:
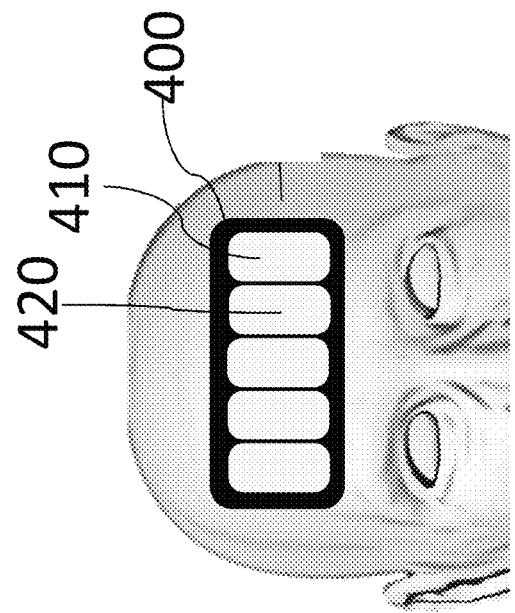
FIG. 22C is an illustration of a stamping mode operation of the applicator of FIG. 22B according to some embodiments of the invention.
Figure 22B:
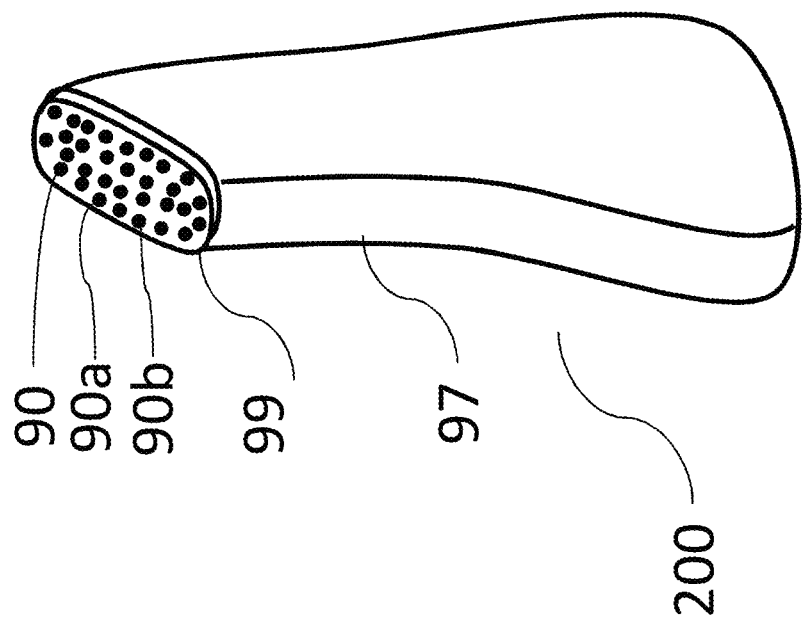

FIG. 22B is an illustration of a moving applicator in a stamping mode for achieving desired impact of breast lifting or any other tissue treatment. Applicator 200 may be included in a hand-piece, which may include of a grip 97 and shaped treatment surface portion 99. The treatment surface portion 99 may be composed of electrically isolated non-conductive material, having array of electrodes 90, 90a, 90b. The applicator components and paired-electrode orientation concepts may be similar to those of the roller configuration presented in FIG. 22A with the necessary adjustments. Treatment according to this embodiment may be carried out in a stamping mode, as illustrated in FIG. 22 C. Tissue 400 may be treated by moving applicator 200 from one stamping position 410 to an adjacent stamping position 420. At each applicator position (e.g., 410, 420) on tissue 400 ('stamping') an area similar to the applicator treatment surface may be treated to form elongated heated volumes (e.g., volumes 10) of predetermined orientation. Treatment may be conducted by put-and-stamp area 410 then moving the applicator to adjacent area 420 for an additional put-and-stamp and so on until covering the entire treated tissue 400 surface in the predetermined orientation. Fine tuning of the orientation of the elongated treated volumes at each applicator positions may be done by rotating treatment surface portion 99 once the applicator is positioned on the surface before activating the RF, based on orientation sensor 98. The treatment surface portion may be disposable.

In some embodiments, applicator 200 and/or apparatus 70 may further include a motion sensor for monitoring the motion of the apparatus and/or applicator with respect to the treated tissue.

Figure 23A:
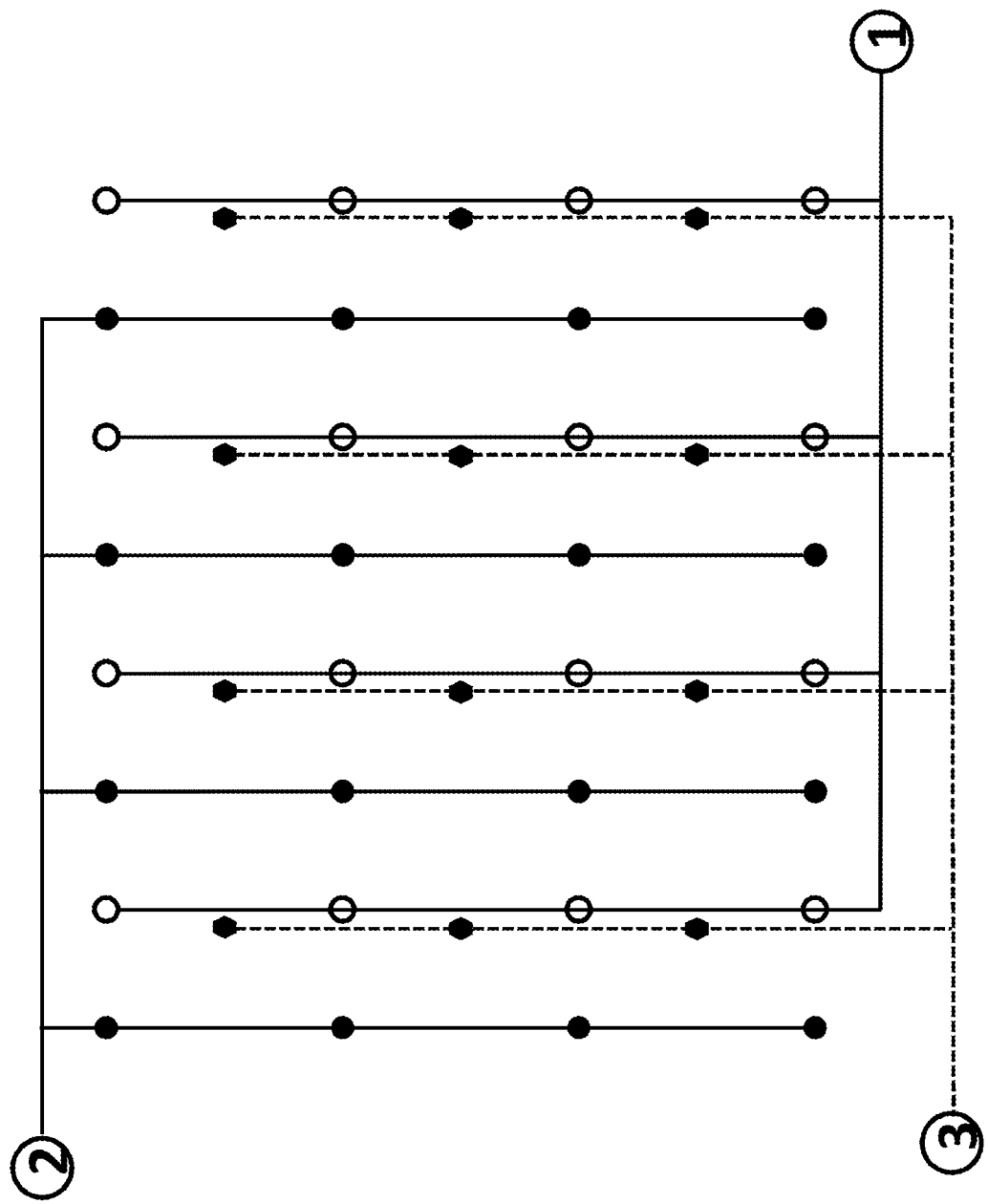

FIG. 23A is an illustration of a one non-limiting embodiment of part of the electrodes array where the electrodes' array is divided into 3 interlaced sub arrays each can be connected to an electrical polarity. FIG. 23B is a schematic of the same array presented in FIG. 23A where one array 1083 is electrically disconnected. The 2 remaining activated sub arrays may be connected to have a lateral horizontal electrical current flow 1080 and its derived heat impact between positive 1082 and negative 1081 electrodes (e.g., included in RF delivery elements), in the tissue.

This connection of activation of electrical branches 1 and 2 may be done when treating the lower quarters of the breast. FIG. 23C is another schematic of the array presented in FIG. 23A where the sub arrays of electrical branches 1 and 3, and related positively and negatively charged electrodes may be connected, while one electrical branch 1085 may be disconnected. The activated sub arrays of the positively charged electrodes 1086 and the negatively charged electrodes 1087 may be connected to have a vertical electrical current flow 1088 and its derived heat impact in the tissue. Such electrical connection may be activated when treating the upper quarters of the breast.

The activation of the required electrodes sub arrays may be done either electronically or mechanically. For the roller applicator, the activation of the required electrodes sub arrays may be based on the orientation of the roller's surface being in contact with the skin. If the roller's surface that being active with the skin is facing down, then at this moment the upper breast quarter may be treated. If the roller's surface being in contact with the skin is facing up, then at this moment the lower breast quarter is being treated. For orientations that might be ambiguous on whether upper or lower quarter may be in contact with the roller's surface. An algorithm based on the orientations history may be used to remove the ambiguity.

In some embodiments, the penetration depth of the RF current may be dependent on known factors such as distance between electrodes or RF frequency. Therefore, at a primary level, the inter-electrode distance may be set to control the depth of treatment. In some embodiments, an effective penetration depth of the RF current may be the depth where a significant percentage of the RF energy can efficiently impact (e.g., heat) the tissue. An exemplary calculation of the effective depth being affected by RF current may result in that the effective depth may be half the distance between electrode's pair or the dimension of the monopolar electrode. For example, to confine the impacting heat to a depth of 2 mm the distance between adjacent opposite polarities RF electrodes should be 4 mm. This calculation may allow targeting the heating of tissue to desired portions such as the dermis and fascia depth levels, and to avoid undesired heating of deeper fat and glandular portions of the breast.

For each inter electrode distance RF frequency may be tuned to further control the effective depth.

According to some embodiments, the distance between electrodes or the dimension or the electrodes may be adapted to the breast or other treated anatomies skin thickness. RF frequency tuning may be conducted electrically, e.g. by RF generator 310 (in FIG. 17A).

According to some embodiments, pretreatment measurement of the skin thickness may be done based on impedance difference between tissues' types.

Figure 24A:
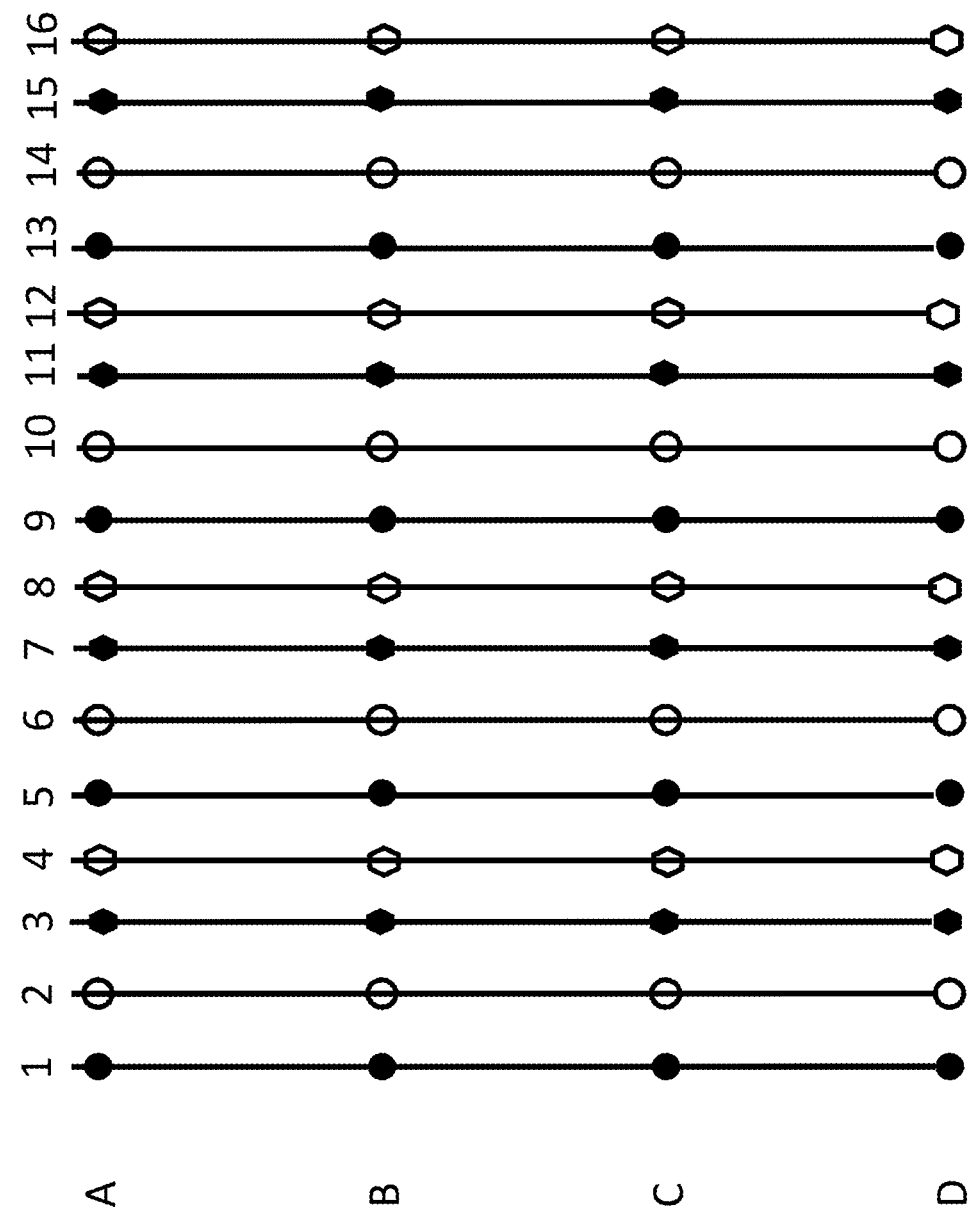
FIGS. 24A and 24B are illustrations of electrodes arrays for supporting different tissue thickness according to some embodiments of the invention.

In some embodiments, the adaptation of electrode spacing to the skin thickness may be done in various ways. FIG. 24A is an illustration of an electrode array that is constructed with very short spacing (d) between adjacent electrodes. Short distance spacing may be defined as spacing shorter than the heat dissipation distance in a tissue per the treatment time. This small distance may be designed to limit the treatment depth when treating the minimum breast skin thickness. For example, in order to achieve this depth limit RF generator may activate for each electrode row (e.g., rows A, B, C, D) every adjacent electrode in alternating polarity, e.g., every even electrode in one polarity and every odd electrode with the other polarity. For thicker skin areas, longer distance electrodes may be paired. For example, only odd electrodes may be used where each (1+4i (i is an integer)) electrode in a row may be connected to one polarity and each (3+4i) electrode in a row may be connected to the other polarity. Other combinations of pairing electrodes may be used.

In some embodiments, the pairing may be done before treatment and may be different for different anatomies and different treatment protocols, for example, different pairing may be used for the upper and lower breast's anatomic poles. In other embodiments, the pairing may be done dynamically during treatment to be adapted to local skin thickness.

Figure 24B:
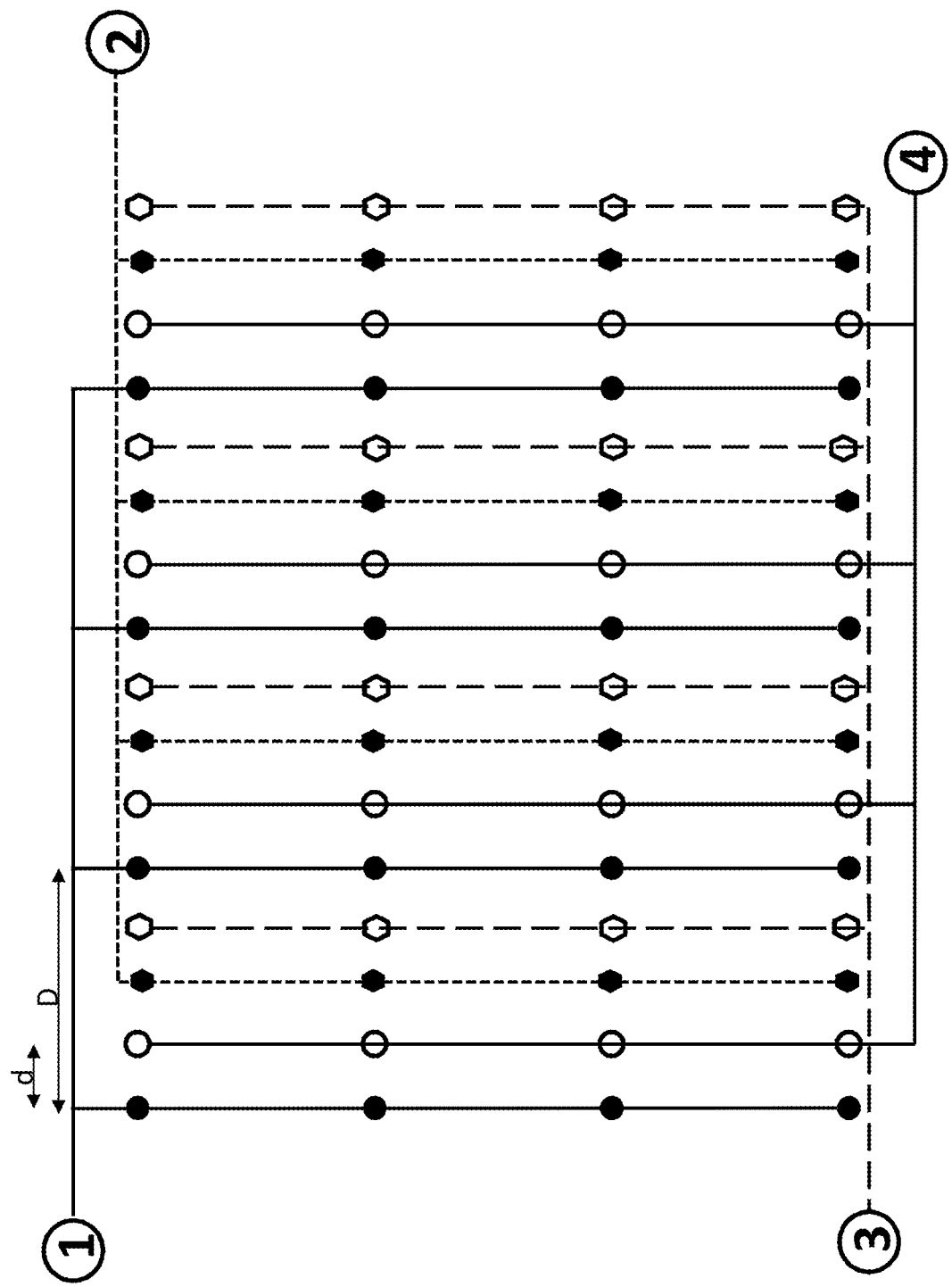

FIG. 24B is an illustration of another embodiment disclosing a plurality of electrodes arrays (1, 2, 3 and 4) each having a first inter-electrode distance D, arrays 1, 2, 3 and 4 may be interlaced in each other so that a second distance (d) between one electrode of a first array and another proximal electrode of a second proximal array may shorter than inter-electrode distance D of each of arrays 1, 2, 3 and 4. Electrodes' pairing may be done based on skin thickness. One can activate array "1" at one polarity and array "2" at another polarity without connecting arrays 3 and 4 to achieve active pairs distance of "2d", or Arrays "1" and "2" can be connected to the same polarity and connecting arrays "3" and "4" to the opposite polarity to achieve active pairs distance "d".

In another embodiment, adaptation to skin thickness may be done by attaching or sticking a sheath or flexible printed circuit board with the suitable electrode size and spacing to applicator (200 in FIGS. 22A and 22B) surface.

In another embodiment, a roller with embedded electrodes may be included in a replaceable unit and may be replaced by another unit having different electrodes spacing and size according to the treatment requirements.

Figure 25:
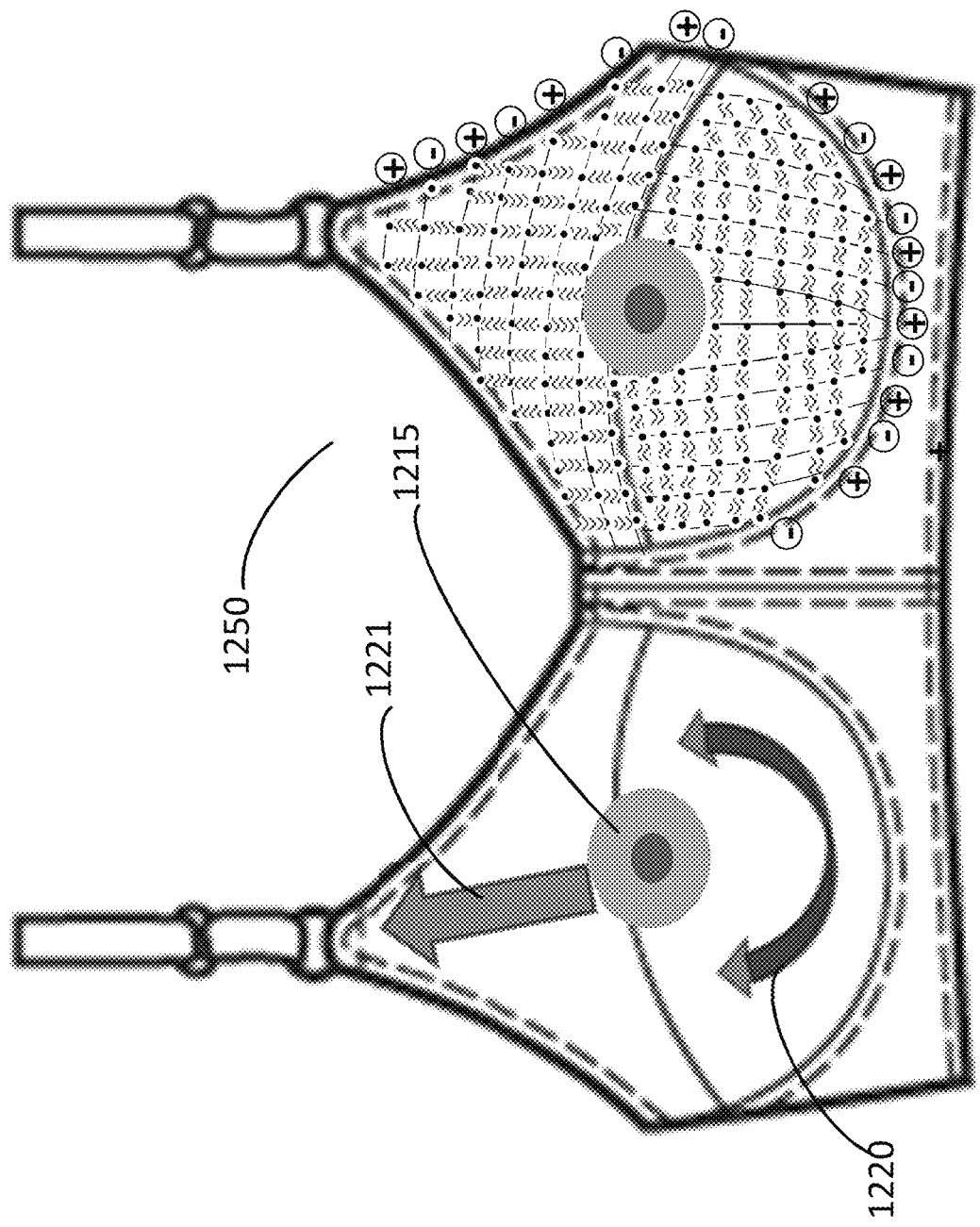
FIG. 25 is an illustration of wearable applicator, designed as a bra, for achieving a desired impact according to some embodiments of the invention.

FIG. 25 is a schematic illustration of wearable applicator, designed as a bra, for achieving a desired impact according to some embodiments of the invention.

In FIG. 25 electrodes are shown only in a left bra 1250 (for ease of explanation) but may be implemented in the right bra in a similar manner.

According to some embodiments, the RF electrodes covering the lower breast quarters may be positioned in such a way to create elongated heat volumes aligned with their long dimension in the lateral general direction. This may result in skin tightening of the lower breast quarters in the overall direction of arrow 1220 and therefore lifting the breast mass in the overall direction of arrow 1221.

According to some embodiments, the RF electrodes covering the upper breast quarters of the breast may be positioned in such a way to create elongated heat volumes aligned with their long dimension in the vertical general direction. This may result in tightening of the upper breast quarters in the overall direction of arrow 1221 and therefore further lifting the breast mass and the nipple and areola. The nipples area 1215, lacking underneath fat support, may not be wired.

The design of bra-applicator 1250 may ensure sufficient contact between the electrodes and the skin for the delivery of a required amount of RF energy to the breast tissue.

In some embodiments, bra 1250 may be manufactured in several sizes to fit different breast sizes.

In one embodiment bra 1250 may be made of silicone gel with embedded electrodes that stick to the breast skin. According to some embodiments, this bra may cover the whole breast surface that is to be treated.

In another embodiment bra 1250 may include at least an outer layer made from any textile material and at least an inner layer made from silicone gel or other material that ensures contact with the breast skin. According to some embodiments, the electrodes may be embedded in the inner layer or any other additional layer. Electrical coupling with the skin may be ensured using gel, or different coupling media.

In yet another embodiment the electrodes may be printed on at least one sheath or on at least one flexible printed circuit board that may be attached or stuck to the inner bra surface and or to the breast skin.

Electrodes' sheath, according to some embodiments, may be replaceable, and/or may be configurable to support different breast sizes, ptosis levels or skin thickness.

According to some embodiments, the electrode array may also be a disposable unit that may be replaced, for example, every new treatment session while the other product components that may be more expensive and are not with direct contact with the body may be reused. The electrode sheath may be electrically connected to the RF generator (310 in FIG. 17A).

Since batteries may have limited electrical current supply, the system controller may activate subsets of electrodes sequentially until covering the whole surface to be treated per the treatment protocol. This sequential operation may ensure operation within the batteries drive current limits. Unless explicitly stated, the method embodiments described herein are not constrained to a particular order in time or chronological sequence. Additionally, some of the described method elements may be skipped, or they may be repeated, during a sequence of operations of a method.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

Various embodiments have been presented. Each of these embodiments may of course include features from other embodiments presented, and embodiments not specifically described may include various features described herein.

What is claimed is:

1. An apparatus for non-invasive directional tissue treatment comprising:
   a two-dimensional array of energy delivery elements placed in a predetermined order defining a tissue treatment area, said array having a first direction and a second direction transverse to the first direction;
   a power source; and
   a controller,
   wherein each of the energy delivery elements is configured to heat a portion of tissue volume within the tissue treatment area and each said energy delivery element has a dimension in the first direction and in the second direction; wherein
   the predetermined order of positioning each energy delivery element is such that a density of treatment energy delivery elements dimensions in the array is higher in the first direction than the density of the energy delivery element dimensions in the second direction; and
   wherein, applying energy to the two-dimensional array is configured to heat tissue in at least one portion of tissue treatment volume; and
   wherein tissue tightening is higher in the first direction than in the second direction of the two-dimensional array.

2. The apparatus according to claim 1, wherein the energy delivery elements are light, microwave or ultrasound elements.

3. The apparatus according to claim 1, wherein each delivery element is elongated in the first direction, configured to heat an elongated tissue volume in the tissue treatment area.

4. The apparatus according to claim 1, wherein each energy delivery element comprises multiple energy delivery sub-elements adapted to heat at least one tissue treatment volume, and wherein said multiple energy delivery sub-elements together define said treatment volume dimensions in said first direction and said second direction.

5. The apparatus according to claim 1, wherein the two-dimensional array comprises at least a first group of energy delivery elements configured to heat a first group of volume portions of tissue, said energy delivery elements dimensions have a first density in the first direction.

6. The apparatus according to claim 5, wherein the two-dimensional array comprises at least a second group of energy delivery elements configured to heat a second group of volume portions of tissue, said second group of energy delivery elements dimension having a second density in the first direction which is different from the first density of tissue treatment volume dimensions of the first group of energy delivery elements in the first direction.

7. The apparatus according to claim 1, wherein the energy delivery elements in the array are arranged in rows and columns.

8. The apparatus according to claim 1, wherein a first distance between first and second energy delivery elements in the two-dimensional array is different from a second distance between second and third energy delivery elements, in the two-dimensional array.

9. The apparatus according to claim 1, wherein the two-dimensional array comprises at least a first group of energy delivery elements located at a first area and a second group of energy delivery elements located at a second area, different from said first area, and wherein a density of energy delivery element dimensions in a first direction in the first area is different from a density of energy delivery element dimensions in the second area.

10. The apparatus according to claim 9, wherein the patch is in a bra configuration, and wherein the two-dimensional array comprises at least two sub arrays, wherein the first sub array is configured to heat a first group of elongated volume portions of tissue having a first orientation and wherein the second sub array is configured to heat a second group of elongated volume portions of tissue having a second orientation different from the first orientation,
    wherein, the first orientation is configured to cause tightening of a lower breast pole in a lateral direction and the second orientation is configured to cause tightening and lifting of an upper breast pole in a vertical direction.

11. The apparatus according to claim 10, wherein the processor is further configured to analyze the received images to determine required treatment parameters, and to create a 3D model of the tissue treatment area.

12. The apparatus according to claim 1, further comprising an applicator in a form of a patch, wherein the patch is configured to suit an anatomy of the treatment area, and wherein the two-dimensional array is configured according to the anatomy and a predetermined tightening direction.

13. The apparatus according to claim 1, further comprising a computing device in active communication with the controller, the computing device comprising:
    an imager, configured to capture one or more images of an area of the tissue to be treated;
    at least one input device configured to receive instructions from a user; and
    a processor, configured to receive the images captured by the imager and the instructions received via the input device and to create a treatment protocol.

14. A method of non-invasive directional tissue tightening comprising:
    setting a treatment protocol;
    attaching a two-dimensional array of energy delivery elements to a tissue treatment area of a subject, said two-dimensional array having a first direction and a second direction transverse to the first direction;
    wherein each energy delivery element having dimensions in said first and second directions;
    supplying power to said energy delivery elements from a power source to heat at least one volume portion of tissue in the said treatment area;
    with the controller, activating and deactivating the energy delivery elements in accordance with the treatment protocol,
    wherein each energy delivery element is positioned such that the density of the energy delivery elements dimensions in the array is higher in the first direction than the energy delivery elements dimensions in the second direction;
    and wherein the treatment protocol and the position of the energy delivery elements are configured so that tissue tightening is higher in the first direction than in the second direction.

15. The method according to claim 14, wherein the setting of the treatment protocol comprises:
    capturing, by an imager, at least one image of the tissue treatment area;
    analyzing the at least one image to determine required treatment;
    measuring at least one tissue characteristics; and
    determining the treatment protocol based on the required treatment, and the at least one tissue characteristic.

16. The method according to claim 14, wherein the tissue characteristics is selected from the group consisting of: tissue type, tissue thickness, tissue temperature, and tissue impedance.

17. The method according to claim 14, further comprising:
- selecting, by the controller, two or more sub-groups of energy delivery elements in the two-dimensional array;
- applying a first set of energy delivery parameters to a first sub-group of energy delivery elements; and
- applying a second set of energy delivery parameters to a second group of delivery elements, wherein the first set of energy delivery parameters is different from the second set of energy delivery parameters.

18. The method of claim 14, wherein said energy delivery elements are adapted to deliver light, microwave, ultrasound, mechanical, or heat energy to one or more tissue treatment volumes.

\* \* \* \* \*